(12) United States Patent
Hong et al.

(10) Patent No.: US 11,484,477 B2
(45) Date of Patent: Nov. 1, 2022

(54) DENTAL ADHESIVE MATERIAL KIT

(71) Applicant: KURARAY NORITAKE DENTAL INC., Kurashiki (JP)

(72) Inventors: Ling Hong, Tokyo (JP); Shumei Ishihara, Tokyo (JP); Nobusuke Kashiki, Aichi (JP)

(73) Assignee: KURARAY NORITAKE DENTAL INC., Kurashiki (JP)

( * ) Notice: Subject to any disclaimer, the term of this patent is extended or adjusted under 35 U.S.C. 154(b) by 82 days.

(21) Appl. No.: 16/955,888

(22) PCT Filed: Dec. 20, 2018

(86) PCT No.: PCT/JP2018/047069
§ 371 (c)(1),
(2) Date: Jun. 19, 2020

(87) PCT Pub. No.: WO2019/124515
PCT Pub. Date: Jun. 27, 2019

(65) Prior Publication Data
US 2021/0015716 A1    Jan. 21, 2021

(30) Foreign Application Priority Data
Dec. 21, 2017 (JP) .............................. JP2017-245056

(51) Int. Cl.
A61K 6/853 (2020.01)
A61K 6/896 (2020.01)
A61K 6/58 (2020.01)
A61K 6/62 (2020.01)

(52) U.S. Cl.
CPC ................ *A61K 6/896* (2020.01); *A61K 6/58* (2020.01); *A61K 6/62* (2020.01)

(58) Field of Classification Search
CPC .................................................... A61K 6/853
See application file for complete search history.

(56) References Cited

U.S. PATENT DOCUMENTS

| | | |
|---|---|---|
| 2010/0130682 A1 | 5/2010 | Hinamoto et al. |
| 2014/0134362 A1* | 5/2014 | Iwase .................. G03F 7/0755 428/35.4 |
| 2017/0135909 A1 | 5/2017 | Takei et al. |
| 2019/0000722 A1 | 1/2019 | Suzuki |
| 2019/0262240 A1 | 8/2019 | Kawana et al. |

FOREIGN PATENT DOCUMENTS

| | | |
|---|---|---|
| EP | 3 530 257 A1 | 8/2019 |
| JP | 2002-255721 A | 9/2002 |
| JP | 2009-167132 A | 7/2009 |
| JP | 2011-213514 A | 10/2011 |
| WO | WO 2008/087977 A1 | 7/2008 |
| WO | WO 2013/046648 A1 | 4/2013 |
| WO | WO 2015/190100 A1 | 12/2015 |
| WO | WO 2017/104128 A1 | 6/2017 |
| WO | WO 2018/074594 A1 | 4/2018 |
| WO | WO 2018/074600 A1 | 4/2018 |

OTHER PUBLICATIONS

International Search Report dated Apr. 2, 2019 in PCT/JP2018/047069 filed Dec. 20, 2018, citing documents AB, AN, and AP-AS therein, 2 pages.
Extended European Search Report dated Jul. 26, 2021 in European Patent Application No. 18892219.9, citing documents AO therein, 9 pages.

* cited by examiner

*Primary Examiner* — Benjamin J Packard
(74) *Attorney, Agent, or Firm* — Oblon, McClelland, Maier & Neustadt, L.L.P.

(57) ABSTRACT

The present invention provides a dental adhesive material kit that exhibits high adhesive property to tooth structure and dental prosthesis through photopolymerization while maintaining good ease of handling with the paste properties that undergo little change during long storage. The present invention relates to a dental adhesive material kit comprising:
an aqueous adhesive dental composition (X) comprising a radical polymerizable monomer (a) containing an acidic group, a polymerization accelerator (b), water (c), and a radical polymerizable monomer (d) containing no acidic group; and
a curable dental composition (Y) comprising a hydrophilic radical polymerizable monomer (d-1) containing no acidic group, a hydrophobic radical polymerizable monomer (d-2) containing no acidic group, a chemical polymerization initiator (e), a photopolymerization initiator (f), and a filler (g), the filler (g) being a filler treated with a surface treatment agent, and having an average particle diameter of 0.01 to 50.0 μm,
the surface treatment agent comprising a silane coupling agent (A) represented by general formula [1], and an organosilazane (B) represented by general formula [2].

15 Claims, No Drawings

DENTAL ADHESIVE MATERIAL KIT

TECHNICAL FIELD

The present invention relates to a dental adhesive material kit comprising an aqueous adhesive dental composition and a curable dental composition.

BACKGROUND ART

For dental restoration, a prosthesis, also called an inlay or a crown, fabricated from materials, for example, such as metals or ceramics is secured to a dysfunctional tooth resulting from decay, accidents, or other causes. A dental restoration practice that is also common is aesthetic restorative treatment, in which a veneer—a wafer-thin prosthesis fabricated from material such as ceramic—is secured to a ground tooth surface to improve the color or shape of the tooth. These prostheses are cemented to teeth using a dental adhesive material, or a dental cement as it is also called.

Typically, a dental cement is a paste-like polymerizable and curable dental composition comprised of components such as a radical polymerizable monomer, a filler, and a polymerization initiator, and can be broadly divided into a two-pack dual-cure type containing a chemical polymerization initiator and a photopolymerization initiator as polymerization initiators, and a one-pack photopolymerization type containing only one kind of photopolymerization initiator.

An advantage of the dual-cure type is that it is easily applicable also for bonding of a low light-transmissive prosthesis such as a metal. A downside, however, is that chemical polymerization starts as soon as the two components are mixed, and there is not enough time to make adjustments for positioning of the prosthesis. On the other hand, the photopolymerization type does not require mixing of components, and affords enough time for the procedure because curing does not start until light is applied. This makes the photopolymerization type more favorable for bonding of a high light-transmissive prosthesis such as a veneer.

It is known practice to add a filler to a dental cement to improve spreadability of the paste and the mechanical strength after curing, and a dental cement is used after a surface treatment with a known surface treatment agent such as a silane coupling agent. The surface treatment improves spreadability by improving the affinity between the filler and a radical polymerizable monomer, and the mechanical strength improves as a result of the improved affinity increasing the filling rate of the filler.

It is also known to apply a pretreatment agent, called a primer, to a tooth structure or a prosthesis as a pretreatment of bonding by a dental cement. The primer contains components such as a radical polymerizable monomer containing an acidic group, a radical polymerizable monomer containing no acidic group, and water, and improves the adhesive property of a dental cement to a tooth structure by altering the surface of the tooth structure. With a primer containing a polymerization initiator and a polymerization accelerator, a dental cement can further improve its adhesive property with the radicals generated on the tooth surface and accelerating the rate of polymerization and curing on the tooth surface. While the photopolymerization-type dental cement offers a procedural advantage with enough time afforded for the procedure, a restorative filling treatment using a photopolymerization-type dental cement applies light from above the dental cement, and the dental cement starts curing from the top. This involves the risk of a restorative filling material coming off as a result of concentrated strain and stress occurring at the cement-tooth interface following contraction due to polymerization. Against this backdrop, there has been development of a dual-cure type dental cement that takes into account and seeks to avoid the risk of detachment of a restorative filling material. The dental adhesive material kits described in Patent Literatures 1 and 2 are examples of such a dual-cure type dental cement.

In the dental adhesive material kit described in Patent Literature 1, a transition metal compound is added to an aqueous adhesive dental composition, and hydroperoxide is added to a curable dental composition, without adding an amine to the aqueous adhesive dental composition. The dental adhesive material kit of this related art is an example of a dual-cure type dental cement achieving high bond strength to tooth structure and providing storage stability for the aqueous adhesive dental composition.

In the dental adhesive material kit described in Patent Literature 2, a vanadium compound is added to an aqueous adhesive dental composition, hydroperoxide is added to a curable dental composition, and the aqueous adhesive dental composition contains an amino group-containing (meth)acrylic polymerizable monomer. The dental adhesive material kit of this related art is an example of a dual-cure type dental cement providing desirable storage stability for the aqueous adhesive dental composition, and desirable bond durability for the tooth structure.

CITATION LIST

Patent Literature

Patent Literature 1: JP 2009-167132 A
Patent Literature 2: WO 2017/104128 A1

SUMMARY OF INVENTION

Technical Problem

After studies, the present inventors found that the dental adhesive material kits disclosed in Patent Literatures 1 and 2 need further improvements in terms of ease of handling because the paste properties of the curable dental composition undergo large changes during long storage. It was also found that photocurability, and the bond strength after long storage decrease as a result of degradation of the photopolymerization initiator when the photopolymerization initiator is in coexistence with a basic filler and a peroxide.

It is accordingly an object of the present invention to provide a dental adhesive material kit comprising an aqueous adhesive dental composition and a curable dental composition, and that exhibits high adhesive property to tooth structure and dental prosthesis through photopolymerization while maintaining good ease of handling with the paste properties that undergo little change during long storage.

Solution to Problem

Specifically, the present invention provides the following.
[1] A dental adhesive material kit comprising an aqueous adhesive dental composition (X) and a curable dental composition (Y),
the aqueous adhesive dental composition (X) comprising a radical polymerizable monomer (a) containing an acidic group, a polymerization accelerator (b), water (c), and a radical polymerizable monomer (d) containing no acidic group, the curable dental composition (Y) comprising a hydrophilic radical polymerizable monomer (d-1) containing no acidic group, a hydrophobic radical polymerizable monomer (d-2) containing no acidic group, a chemical polymerization initiator (e), a photopolymerization initiator (f), and a filler (g), the filler (g) being a filler treated with a surface treatment agent, and having an average particle diameter of 0.01 to 50.0 μm, the surface treatment agent comprising:

a silane coupling agent (A) represented by the following general formula [1], $$CH_2=C(R^1)-COO-(CH_2)_p-Si-R^2_qR^3_{(3-q)} \quad [1],$$

where $R^1$ is a hydrogen atom or a methyl group, $R^2$ is an optionally substituted hydrolyzable group, $R^3$ is an optionally substituted $C_1$ to $C_3$ alkyl group, p is an integer of 1 to 13, and q is 2 or 3, and an organosilazane (B) represented by the following general formula [2], $$R^4R^5R^6-Si-NH-Si-R^7R^8R^9 \quad [2],$$

where $R^4$, $R^5$, and $R^6$ each independently represent a hydrogen atom or an optionally substituted $C_1$ to $C_3$ alkyl group, at least one of $R^4$, $R^5$, and $R^6$ being an optionally substituted $C_1$ to $C_3$ alkyl group, and $R^7$, $R^8$, and $R^9$ each independently represent a hydrogen atom or an optionally substituted $C_1$ to $C_3$ alkyl group, at least one of $R^7$, $R^8$, and $R^9$ being an optionally substituted $C_1$ to $C_3$ alkyl group.

[2] The dental adhesive material kit of item [1], wherein $R^2$ is an unsubstituted hydrolyzable group, $R^3$ is an unsubstituted $C_1$ to $C_3$ alkyl group, $R^4$, $R^5$, and $R^6$ each independently represent a hydrogen atom or an unsubstituted $C_1$ to $C_3$ alkyl group, at least one of $R^4$, $R^5$, and $R^6$ being an unsubstituted $C_1$ to $C_3$ alkyl group, and $R^7$, $R^8$, and $R^9$ each independently represent a hydrogen atom or an unsubstituted $C_1$ to $C_3$ alkyl group, at least one of $R^7$, $R^8$, and $R^9$ being an unsubstituted $C_1$ to $C_3$ alkyl group.

[3] The dental adhesive material kit of item [1] or [2], wherein $R^2$ is an unsubstituted $C_1$ to $C_6$ linear or branched alkoxy group.

[4] The dental adhesive material kit of any one of items [1] to [3], wherein $R^1$ is a methyl group.

[5] The dental adhesive material kit of any one of items [1] to [4], wherein p is 2 to 10.

[6] The dental adhesive material kit of any one of items [1] to [5], wherein q is 3.

[7] The dental adhesive material kit of any one of items [1] to [6], wherein the silane coupling agent (A) is at least one selected from the group consisting of 2-(meth)acryloxyethyltrimethoxysilane, 3-(meth)acryloxypropyltrimethoxysilane, 4-(meth)acryloxybutyltrimethoxysilane, 5-(meth)acryloxypentyltrimethoxysilane, and 6-(metWacryloxyhexyltrimethoxysilane.

[8] The dental adhesive material kit of any one of items [1] to [7], wherein the organosilazane (B) is at least one selected from the group consisting of 1,1,3,3-tetramethyldisilazane, 1,1,1,3,3,3-hexamethyldisilazane, and 1,1,1,3,3-pentamethyldisilazane.

[9] The dental adhesive material kit of any one of items [1] to [8], wherein the silane coupling agent (A) and the organosilazane (B) have a silane coupling agent (A):organosilazane (B) mole ratio of 1:1 to 1:20.

[10] The dental adhesive material kit of any one of items [1] to [9], wherein the radical polymerizable monomer (d) containing no acidic group comprises a hydrophilic radical polymerizable monomer (d-1) containing no acidic group.

[11] The dental adhesive material kit of any one of items [1] to [10], wherein the hydrophilic radical polymerizable monomer (d-1) containing no acidic group contained in the curable dental composition (Y) comprises a monofunctional (meth)acrylamide hydrophilic radical polymerizable monomer containing no acidic group.

[12] The dental adhesive material kit of any one of items [1] to [11], wherein the polymerization accelerator (b) is a period 4 transition metal compound (b-3).

[13] The dental adhesive material kit of any one of items [1] to [12], wherein the chemical polymerization initiator (e) is a hydroperoxide.

[14] The dental adhesive material kit of any one of items [1] to [13], wherein the curable dental composition (Y) is a one-pack curable dental composition.

[15] The dental adhesive material kit of any one of items [1] to [14], wherein the kit is a dental veneer cement kit.

Advantageous Effects of Invention

The present invention provides a dental adhesive material kit comprising an aqueous adhesive dental composition and a curable dental composition, and that exhibits high adhesive property to tooth structure and dental prosthesis through photopolymerization while maintaining good ease of handling with the paste properties that undergo little change during long storage. A dental adhesive material kit of the present invention ensures desirable mechanical strength for the cured product of the curable dental composition.

DESCRIPTION OF EMBODIMENTS

A dental adhesive material kit of the present invention is a dental adhesive material kit comprising an aqueous adhesive dental composition (X) and a curable dental composition (Y), the aqueous adhesive dental composition (X) comprising a radical polymerizable monomer (a) containing an acidic group, a polymerization accelerator (b), water (c), and a radical polymerizable monomer (d) containing no acidic group, the curable dental composition (Y) comprising a hydrophilic radical polymerizable monomer (d-1) containing no acidic group, a hydrophobic radical polymerizable monomer (d-2) containing no acidic group, a chemical polymerization initiator (e), a photopolymerization initiator (f), and a filler (g), the filler (g) being a filler treated with a surface treatment agent, and having an average particle diameter of 0.01 to 50.0 μm, the surface treatment agent comprising:

a silane coupling agent (A) represented by the following general formula [1], $$CH_2=C(R^1)-COO-(CH_2)_p-Si-R^2_qR^3_{(3-q)} \quad [1],$$

where $R^1$ is a hydrogen atom or a methyl group, $R^2$ is an optionally substituted hydrolyzable group, $R^3$ is an optionally substituted $C_1$ to $C_3$ alkyl group, p is an integer of 1 to 13, and q is 2 or 3, and an organosilazane (B) represented by the following general formula [2], $$R^4R^5R^6-Si-NH-Si-R^7R^8R^9 \quad [2],$$

where $R^4$, $R^5$, and $R^6$ each independently represent a hydrogen atom or an optionally substituted $C_1$ to $C_3$ alkyl group, at least one of $R^4$, $R^5$, and $R^6$ being an optionally substituted $C_1$ to $C_3$ alkyl group, and $R^7$, $R^8$, and $R^9$ each independently represent a hydrogen atom or an optionally substituted $C_1$ to $C_3$ alkyl group, at least one of $R^7$, $R^8$, and $R^9$ being an optionally substituted $C_1$ to $C_3$ alkyl group.

In the present specification, the upper limits and lower limits of numeric ranges (for example, ranges of contents of components, ranges of values calculated from components, ranges of values of physical properties, and ranges of numeric values represented by symbols in various formulae) can be combined appropriately.

Aqueous Adhesive Dental Composition (X)

The aqueous adhesive dental composition (X) is described below in detail. The aqueous adhesive dental composition (X) of the present invention comprises a radical polymerizable monomer (a) containing an acidic group. The radical polymerizable monomer (a) containing an acidic group promotes demineralization of a tooth structure, and improves adhesive property to tooth structure by penetrating into a tooth structure and forming a chemical bond with the calcium in the tooth structure. The radical polymerizable monomer (a) containing an acidic group also improves adhesive property to dental prostheses. As used herein, "(meth)acryl" is meant to be inclusive of both "methacryl" and "acryl", and "(meth)acryloyl" is meant to be inclusive of both "methacryloyl" and "acryloyl".

The radical polymerizable monomer (a) containing an acidic group is, for example, a (meth)acrylic polymerizable monomer having at least one acidic group such as a phosphoric acid group, a pyrophosphoric acid group, a thiophosphoric acid group, a phosphonic acid group, a carboxylic acid group, or a sulfonic acid group, and at least one (meth)acryloyl group. The radical polymerizable monomer (a) containing an acidic group may be used alone, or two or more thereof may be used in combination as appropriate. Specific examples of the radical polymerizable monomer (a) containing an acidic group are as follows.

Examples of the (meth)acrylic polymerizable monomer containing a phosphoric acid group include:

monofunctional phosphoric acid group-containing (meth)acrylic acid esters such as 2-(meth)acryloxyethyl dihydrogen phosphate, 3-(meth)acryloxypropyl dihydrogen phosphate, 4-(meth)acryloxybutyl dihydrogen phosphate, 5-(meth)acryloxypentyl dihydrogen phosphate, 6-(meth)acryloxyhexyl dihydrogen phosphate, 7-(meth)acryloxyheptyl dihydrogen phosphate, 8-(meth)acryloxyoctyl dihydrogen phosphate, 9-(meth)acryloxynonyl dihydrogen phosphate, 10-(meth)acryloxydecyl dihydrogen phosphate, 11-(meth)acryloxyundecyl dihydrogen phosphate, 12-(meth)acryloxydodecyl dihydrogen phosphate, 16-(meth)acryloxyhexadecyl dihydrogen phosphate, 20-(meth)acryloxyeicosyl dihydrogen phosphate, 2-(meth)acryloxyethylphenyl hydrogen phosphate, 2-(meth)acryloxyethyl-2-bromoethyl hydrogen phosphate, 2-(meth)acryloxyethyl-(4-methoxyphenyl)hydrogen phosphate, and 2-(meth)acryloxypropyl-(4-methoxyphenyl)hydrogen phosphate, and acid chlorides, alkali metal salts, and amine salts thereof; and bifunctional phosphoric acid group-containing (meth)acrylic acid esters such as bis[2-(meth)acryloxyethyl]hydrogen phosphate, bis[4-(meth)acryloxybutyl]hydrogen phosphate, bis[6-(meth)acryloxyhexyl]hydrogen phosphate, bis[8-(meth)acryloxyoctyl]hydrogen phosphate, bis[9-(meth)acryloxynonyl]hydrogen phosphate, bis[10-(meth)acryloxydecyl]hydrogen phosphate, and 1,3-di(meth)acryloxypropyl dihydrogen phosphate, and acid chlorides, alkali metal salts, and amine salts thereof.

Examples of the (meth)acrylic polymerizable monomer containing a pyrophosphoric acid group include bis[2-(meth)acryloxyethyl]pyrophosphate, bis[4-(meth)acryloxybutyl]pyrophosphate, bis[6-(meth)acryloxyhexyl]pyrophosphate, bis[8-(meth)acryloxyoctyl]pyrophosphate, and bis[10-(meth)acryloxydecyl]pyrophosphate, and acid chlorides, alkali metal salts, and amine salts thereof.

Examples of the (meth)acrylic polymerizable monomer containing a thiophosphoric acid group include 2-(meth)acryloxyethyl dihydrogen thiophosphate, 3-(meth)acryloxypropyl dihydrogen thiophosphate, 4-(meth)acryloxybutyl dihydrogen thiophosphate, 5-(meth)acryloxypentyl dihydrogen thiophosphate, 6-(meth)acryloxyhexyl dihydrogen thiophosphate, 7-(meth)acryloxyheptyl dihydrogen thiophosphate, 8-(meth)acryloxyoctyl dihydrogen thiophosphate, 9-(meth)acryloxynonyl dihydrogen thiophosphate, 10-(meth)acryloxydecyl dihydrogen thiophosphate, 11-(meth)acryloxyundecyl dihydrogen thiophosphate, 12-(meth)acryloxydodecyl dihydrogen thiophosphate, 16-(meth)acryloxyhexadecyl dihydrogen thiophosphate, and 20-(meth)acryloxyeicosyl dihydrogen thiophosphate, and acid chlorides, alkali metal salts, and ammonium salts thereof.

Examples of the (meth)acrylic polymerizable monomer containing a phosphonic acid group include 2-(meth)acryloxyethylphenyl phosphonate, 5-(meth)acryloxypentyl-3-phosphonopropionate, 6-(meth)acryloxyhexyl-3-phosphonopropionate, 10-(meth)acryloxydecyl-3-phosphonopropionate, 6-(meth)acryloxyhexylphosphonoacetate, and 10-(meth)acryloxydecylphosphonoacetate, and acid chlorides, alkali metal salts, and ammonium salts thereof.

Examples of the (meth)acrylic polymerizable monomer containing a carboxylic acid group include (meth)acrylic polymerizable monomers having one carboxy group or an acid anhydride group thereof within the molecule; and (meth)acrylic polymerizable monomers having a plurality of carboxy groups or acid anhydride groups thereof within the molecule.

Examples of the (meth)acrylic polymerizable monomers having one carboxy group or an acid anhydride group thereof within the molecule include (meth)acrylic acid, N-(meth)acryloylglycine, N-(meth)acryloylaspartic acid, 2-(meth)acryloxyethyl hydrogen succinate, 2-(meth)acryloxyethyl hydrogen phthalate, 2-(meth)acryloxyethyl hydrogen malate, O-(meth)acryloyltyrosine, N-(meth)acryloyltyrosine, N-(meth)acryloylphenylalanine, N-(meth)acryloyl-p-aminobenzoic acid, N-(meth)acryloyl-o-aminobenzoic acid, 2-(meth)acryloxybenzoic acid, 3-(meth)acryloxybenzoic acid, 4-(meth)acryloxybenzoic acid, N-(meth)acryloyl-5-aminosalicylic acid, and N-(meth)acryloyl-4-aminosalicylic acid, and compounds derived by converting the carboxy group of the aforementioned compounds into an acid anhydride group.

Examples of the (meth)acrylic polymerizable monomers having a plurality of carboxy groups or acid anhydride groups thereof within the molecule include 6-(meth)acryloxyhexane-1,1-dicarboxylic acid, 9-(meth)acryloxynonane-1,1-dicarboxylic acid, 10-(meth)acryloxydecane-1,1-dicarboxylic acid, 11-(meth)acryloxyundecane-1,1-dicarboxylic acid, 12-(meth)acryloxydodecane-1,1-dicarboxylic acid, 13-(meth)acryloxytridecane-1,1-dicarboxylic acid, 4-(meth)acryloxyethyltrimellitate, 4-(meth)acryloxyethyltrimellitate anhydride, 4-(meth)acryloxybutyltrimellitate, 4-(meth)acryloxyhexyltrimellitate, 4-(meth)acryloxydecyltrimellitate, 2-(meth)acryloxyethyl- 3'-(meth)acryloxy-2'-(3,4-dicarboxybenzoyloxy)propylsuccinate, 6-(meth)acryloxyethylnaphthalene-1,2,6-tricarboxylic acid anhydride, 6-(meth)acryloxyethylnaphthalene-2,3,6-tricarboxylic acid anhydride, 4-(meth)acryloxyethylcarbonylpropionoyl-1,8-naphthalic acid anhydride, and 4-(meth)acryloxyethylnaphthalene-1,8-tricarboxylic acid anhydride.

Examples of the (meth)acrylic polymerizable monomer containing a sulfonic acid group include 2-(meth)acrylamide-2-methylpropanesulfonic acid, and 2-sulfoethyl(meth)acrylate.

In view of desirable bond strength, preferred among the aforementioned radical polymerizable monomers (a) containing an acidic group is one or more selected from the group consisting of 10-(meth)acryloxydecyl dihydrogen phosphate, 4-(meth)acryloxyethyltrimellitate anhydride, 4-(meth)acryloxyethyltrimellitate, 11-(meth)acryloxyundecane-1,1-dicarboxylic acid, and a mixture of 2-(meth)acryloxyethyl dihydrogen phosphate and bis(2-(meth)acryloxyethyl)hydrogen phosphate.

The content of the radical polymerizable monomer (a) containing an acidic group in the aqueous adhesive dental composition (X) is preferably 1 to 45 parts by mass, more preferably 5 to 40 parts by mass, even more preferably 10 to 38 parts by mass per 100 parts by mass of the total amount of radical polymerizable monomers and solvent contained in the aqueous adhesive dental composition (X). Here, "total amount of radical polymerizable monomers and solvent" means the combined amount of the radical polymerizable monomer (a) containing an acidic group, polymerization accelerator (b), water (c), organic solvent, polymerization inhibitor, and other polymerizable monomers (for example, radical polymerizable monomer (d) containing no acidic group).

For further improvement of adhesive property to tooth structure and dental prosthesis, the aqueous adhesive dental composition (X) of the present invention comprises a polymerization accelerator (b). The polymerization accelerator (b) is a component that serves as a reducing agent of a redox polymerization initiator. Examples of the polymerization accelerator (b) in the aqueous adhesive dental composition (X) include an aromatic amine (b-1) having no electron withdrawing group in the aromatic ring, a thiourea compound (b-2), and a period 4 transition metal compound (b-3). The polymerization accelerator (b) may be used alone, or two or more thereof may be used in combination.

Examples of the aromatic amine (b-1) having no electron withdrawing group in the aromatic ring include N,N-bis(2-hydroxyethyl)-3,5-dimethylaniline, N,N-bis(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylandine, N,N-bis(2-hydroxyethyl)-3,5-di-isopropylaniline, N,N-bis(2-hydroxyethyl)-3,5-di-t-butylaniline, N,N-dimethylaniline, N,N-dimethyl-p-toluidine, N,N dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, and N,N-dimethyl-3,5-di-t-butylaniline. The aromatic amine (b-1) having no electron withdrawing group in the aromatic ring may be used alone, or two or more thereof may be used in combination.

Examples of the thiourea compound (b-2) include thiourea, methylthiourea, ethylthiourea, ethylenethiourea, N,N'-dimethylthiourea, N,N'-diethylthiourea, N,N'-di-n-propylthiourea, N,N'-dicyclohexylthiourea, trimethylthiourea, triethylthiourea, tri-n-propylthiourea, tricyclohexylthiourea, tetramethylthiourea, tetraethylthiourea, tetra-n-propylthiourea, tetracyclohexylthiourea, 1-(2-pyridyl)-2-thiourea, and 4,4-dimethylethylenethiourea.

The period 4 transition metal compound (b-3) may be any of a vanadium compound (b-3-1), a copper compound (b-3-2), and other period 4 transition metal compounds (b-3-3).

Examples of the vanadium compound (b-3-1) include vanadium acetylacetonate, vanadyl(IV) acetylacetonate, vanadyl stearate, vanadium naphthenate, vanadium benzoylacetonate, vanadyl oxalate, bis(maltolato)oxovanadium (IV), oxobis(1-phenyl-1,3-butanedionate)vanadium(IV), vanadium(V) oxytriisopropoxide, ammonium metavanadate, sodium metavanadate, vanadium(v) oxide, vanadium (IV) oxide, and vanadyl sulfate. In view of properties such as solubility in water (c), vanadium acetylacetonate, vanadyl (IV) acetylacetonate, and bis(maltolato)oxovanadium(IV) are preferred, and vanadyl(IV) acetylacetonate and bis (maltolato)oxovanadium(IV) are more preferred. The vanadium compound (b-3-1) may be used alone, or two or more thereof may be used in combination.

Preferred examples of the copper compound (b-3-2) include compounds that are soluble in the radical polymerizable monomers. Specific examples of such compounds include:

copper carboxylates such as copper acetate, copper isobutyrate, copper gluconate, copper citrate, copper phthalate, copper tartrate, copper oleate, copper octylate, copper octenoate, copper naphthenate, copper methacrylate, and copper 4-cyclohexylbutyrate;

β-diketone-copper such as copper acetylacetonate, copper trifluoroacetylacetonate, copper hexafluoroacetylacetonate, copper 2,2,6,6-tetramethyl-3,5-heptanedionate, and benzoylacetone copper;

β-ketoester-copper such as copper ethylacetoacetate;

copper alkoxides such as copper methoxide, copper ethoxide, copper isopropoxide, copper 2-(2-butoxyethoxy) ethoxide, and copper 2-(2-methoxyethoxy)ethoxide;

copper dithiocarbamates such as copper dimethyldithiocarbamate;

inorganic acid salts of copper such as copper nitrate; and copper chloride.

These may be used alone, or two or more thereof may be used in combination as appropriate. In view of solubility and reactivity to the radical polymerizable monomers, copper carboxylate, β-diketone-copper, and β-ketoester-copper are preferred, and copper acetate and copper acetylacetonate are particularly preferred.

Examples of the other period 4 transition metal compounds (b-3-3) include scandium isopropoxide, yttrium isopropoxide, lanthanum methoxide, lanthanum ethoxide, lanthanum isopropoxide, lanthanum butoxide, lanthanum hydroxide, lanthanum carbonate, lanthanum fluoride, cerium isopropoxide, praseodymium isopropoxide, promethium isopropoxide, neodymium isopropoxide, samarium isopropoxide, europium isopropoxide, gadolinium isopropoxide, terbium ethoxide, terbium methoxide, dysprosium isopropoxide, holmium isopropoxide, erbium isopropoxide, thulium isopropoxide, ytterbium isopropoxide, ethoxide, actinium ethoxide, titanium methoxide, titanium ethoxide, titanium isopropoxide, titanium butoxide, titanium hydroxide, titanium fluoride, zirconium ethoxide, zirconium isopropoxide, zirconium butoxide, tungsten(IV) methoxide, tungsten(IV) isopropoxide, and tungsten(IV) butoxide. Preferred among these period 4 transition metal compounds (b-3) are vanadium(IV) oxide, vanadyl(IV) acetylacetonate, vanadyl oxalate, vanadyl sulfate, vanadium(IV) oxobis(1-phenyl-1,3-butanedionate), bis(maltolato)oxovanadium (IV), vanadium(V) oxide, sodium metavanadate, and ammonium metavanadate. In view of the curability of the composition, preferred as the polymerization accelerator (b) are vanadyl(IV) acetylacetonate and bis(maltolato)oxovanadium(IV), most preferably vanadyl(IV) acetylacetonate.

A slowing of cure rate can be avoided when the content of the polymerization accelerator (b) in the aqueous adhesive dental composition (X) is 0.0001 parts by mass or more per 100 parts by mass of the total amount of radical polymerizable monomers contained in the aqueous adhesive dental composition (X). Accordingly, the content of polymerization accelerator (b) is preferably 0.0001 parts by mass or more, more preferably 0.0005 parts by mass or more, even more preferably 0.001 parts by mass or more. The possibility of dissolution of a polymerization initiator residue from a cured product of aqueous adhesive dental composition (X) can be eliminated when the content of the polymerization accelerator (b) is 10 parts by mass or less per 100 parts by mass of the total amount of radical polymerizable monomers contained in the aqueous adhesive dental composition (X). Accordingly, the content of the polymerization accelerator (b) is preferably 10 parts by mass or less, more preferably 5.0 parts by mass or less, even more preferably 1.0 part by mass or less.

The aqueous adhesive dental composition (X) of the present invention comprises water (c). Water (c) contributes to promoting penetration of the composition into a tooth structure. Water (c) can also serve to dissolve the radical polymerizable monomer (a) containing an acidic group and the polymerization accelerator (b), and may provide a field for the dissolution and reaction of substances that contribute to initiation of polymerization.

The content of water (c) in the aqueous adhesive dental composition (X) is preferably 5 to 74 parts by mass, more preferably 10 to 60 parts by mass, even more preferably 15 to 45 parts by mass per 100 parts by mass of the total amount of radical polymerizable monomers and solvent contained in the aqueous adhesive dental composition (X).

The aqueous adhesive dental composition (X) of the present invention comprises a radical polymerizable monomer (d) containing no acidic group.

The radical polymerizable monomer (d) containing no acidic group means a radical polymerizable monomer that does not contain an acidic group such as a phosphoric acid group, a pyrophosphoric acid group, a thiophosphoric acid group, a phosphonic acid group, a carboxylic acid group, or a sulfonic acid group. The radical polymerizable monomer (d) containing no acidic group may be used alone, or two or more thereof may be used in combination as appropriate.

The radical polymerizable monomer (d) containing no acidic group can be broadly divided into a hydrophilic radical polymerizable monomer (d-1) containing no acidic group and a hydrophobic radical polymerizable monomer (d-2) containing no acidic group.

As used herein, "hydrophilic radical polymerizable monomer" means a radical polymerizable monomer containing no acidic group having a solubility of 5 mass % or more for water at 25° C. The hydrophilic radical polymerizable monomer (d-1) containing no acidic group is preferably one having a solubility of preferably 10 mass % or more, more preferably 30 mass % or more for water at 25° C.

As used herein, "hydrophobic radical polymerizable monomer" means a radical polymerizable monomer containing no acidic group having a solubility of less than 5 mass % for water at 25° C.

The hydrophilic radical polymerizable monomer (d-1) containing no acidic group may be monofunctional (d-1-1), bifunctional (d-1-2), or tri- and higher-functional (d-1-3). As used herein, "monofunctional", "bifunctional", and "tri- and higher-functional" means having one, two, and three or more radical polymerizable groups, respectively.

Examples of the monofunctional hydrophilic radical polymerizable monomer (d-1-1) containing no acidic group include:

monofunctional (meth)acrylic acid ester hydrophilic radical polymerizable monomers such as 2-hydroxyethyl(meth)acrylate, 2-hydroxypropyl(meth)acrylate, 3-hydroxypropyl (meth)acrylate, 1,3-dihydroxypropyl(meth)acrylate, 2,3-dihydroxypropyl(meth)acrylate, 2-hydroxybutyl(meth)acrylate, propylene glycol mono(meth)acrylate, glycerol mono(meth)acrylate, erythritol mono(meth)acrylate, and methoxypolyethylene glycol(meth)acrylate;

monofunctional (meth) acrylamide hydrophilic radical polymerizable monomers such as N-methylogmeth)acrylamide, N-hydroxyethyl(meth)acrylamide, N,N-bis(2-hydroxyethyl)(meth)acrylamide, dimethyl(meth)acrylamide, and diethyl(meth)acrylamide; and (meth)acryloylmorpholine.

Examples of the bifunctional hydrophilic radical polymerizable monomer (d-1-2) containing no acidic group include:

bifunctional (meth)acrylic acid ester hydrophilic radical polymerizable monomers such as erythritol di(meth)acrylate, sorbitol di(meth)acrylate, mannitol di(meth)acrylate, pentaerythritol di(meth)acrylate, dipentaerythritol di(meth)acrylate, triethylene glycol di(meth)acrylate, polyethylene glycol #200 di(meth)acrylate, polyethylene glycol #400 di(meth)acrylate, glycerol di(meth)acrylate, and 1,2-bis(3-(meth)acryloxy-2-hydroxypropoxy)ethane; and bifunctional (meth)acrylamide hydrophilic radical polymerizable monomers such as ethylenebis(meth)acrylamide, propylenebis(meth)acrylamide, butylenebis(meth)acrylamide, N,N'-(dimethyl)ethylenebis(meth)acrylamide, N,N'-diethyl-1,3-propylenebis(meth)acrylamide, bis[2-(2-methyl-(meth)acrylamino)ethoxycarbonyl]hexamethylene diamine, and 2,2,4-trimethylhexamethylene-1,6-bis(meth)acrylamide.

Examples of the tri- and higher-functional hydrophilic radical polymerizable monomer (d-1-3) containing no acidic group include pentaerythritol tri(meth)acrylate, pentaerythritol tetra(meth)acrylate, dipentaerythritol tri(meth)acrylate, dipentaerythritol tetra(meth)acrylate, and dipentaerythritol penta(meth)acrylate.

The hydrophobic radical polymerizable monomer (d-2) containing no acidic group may be monofunctional (d-2-1), bifunctional(d-2-2), or tri- and higher-functional (d-2-3).

Examples of the monofunctional hydrophobic radical polymerizable monomer (d-2-1) containing no acidic group include methyl(meth)acrylate, ethyl(meth)acrylate, propyl (meth)acrylate, isopropyl(meth)acrylate, butyl(meth)acrylate, isobutyl(meth)acrylate, benzyl(meth)acrylate, lauryl (meth)acrylate, 2-(N,N-dimethylamino)ethygmeth)acrylate, 2,3-dibromopropyl(meth)acrylate, propylene glycol mono (meth)acrylate, glycerin mono(meth)acrylate, erythritol mono(meth)acrylate, and N-methylol(meth)acrylamide.

Examples of the bifunctional hydrophobic radical polymerizable monomer (d-2-2) containing no acidic group include 2,2-bis[4-(3-(meth)acryloxy-2-hydroxypropoxy) phenyl]propane, 2,2-bis((meth)acryloxyphenyl)propane, 2,2-bis(4-(meth)acryloxyethoxyphenyl)propane, 2,2-bis(4-(meth)acryloxydiethoxyphenyl)propane, 2,2-bis(4-(meth) acryloxytriethoxyphenyl)propane, 2,2-bis(4-(meth)acryloxytetraethoxyphenyl)propane, 2,2-bis(4-(meth)acryloxypentaethoxyphenyl)propane, 2,2-bis(4-(meth)acryloxypolyethoxyphenyl)propane (a compound having an average number of moles of ethoxy group added of 2.6), 2-(4-(meth)acryloxydiethoxyphenyl)-2-(4-(meth)acryloxyethoxyphenyl)propane, 2-(4-(meth)acryloxydiethoxyphenyl)-2-(4-(meth)acryloxytriethoxyphenyl)propane, 2,2-bis(4-(meth)acryloxypolyethoxyphenyl)propane, 2-(4-(meth)acryloxydipropoxyphenyl)-2-(4-(meth)acryloxytriethoxyphenyl) propane, 2,2-bis(4-(meth)acryloxypropoxyphenyl)propane, 2,2-bis(4-(meth)acryloxydipropoxyphenyl)propane, and N,N'-(2,2,4-trimethylhexamethylene)bis [2-(aminocarboxy) ethan-1-ol]dimethacrylate.

Examples of the tri- and higher-functional hydrophobic radical polymerizable monomer (d-2-3) containing no acidic group include trimethylolpropane tri(meth)acrylate, trimethylolethane tri(meth)acrylate, tetramethylolmethane tri(meth)acrylate, pentaerythritol tetra(meth)acrylate, N,N'-(2,2,4-trimethylhexamethylene)bis [2-(aminocarboxy) propane-1,3-diol]tetramethacrylate, and 1,7-diacryloxy-2,2,6,6-tetraacryloxymethyl-4-oxyheptane.

The radical polymerizable monomer (d) containing no acidic group improves bond strength by penetrating into a tooth structure and improving the strength of the cured product. The radical polymerizable monomer (d) containing no acidic group contained in the aqueous adhesive dental composition (X) comprises preferably the hydrophilic radical polymerizable monomer (d-1) containing no acidic group, more preferably the monofunctional hydrophilic radical polymerizable monomer (d-1-1). In view of penetrability into tooth structure, the monofunctional hydrophilic radical polymerizable monomer (d-1-1) is preferably 2-hydroxyethyl(meth)acrylate, 3-hydroxypropyl(meth)acrylate, glycerol mono(meth)acrylate, erythritol mono(meth)acrylate, methoxypolyethylene glycol(meth)acrylate, (meth)acryloylmorpholine, or diethyl(meth)acrylamide, most preferably 2-hydroxyethylmethacrylate.

The content of the radical polymerizable monomer (d) containing no acidic group in the aqueous adhesive dental composition (X) is preferably 25 to 70 parts by mass, more preferably 28 to 60 parts by mass, even more preferably 30 to 55 parts by mass per 100 parts by mass of the total amount of radical polymerizable monomers and solvent contained in the aqueous adhesive dental composition (X). The effect of adding the radical polymerizable monomer (d) containing no acidic group, specifically, the adhesive property improving effect becomes more prominent when the content of radical polymerizable monomer (d) containing no acidic group is 25 parts by mass or more per 100 parts by mass of the total amount of radical polymerizable monomers and solvent contained in the aqueous adhesive dental composition (X). The aqueous adhesive dental composition (X) can develop its ability to demineralize a tooth structure at a high level without losing the effect of adding radical polymerizable monomer (d) containing no acidic group when the content of radical polymerizable monomer (d) containing no acidic group is 70 parts by mass or less per 100 parts by mass of the total amount of radical polymerizable monomers and solvent contained in the aqueous adhesive dental composition (X).

The aqueous adhesive dental composition (X) of the present invention may comprise a polymerization inhibitor to impart storage stability. With a polymerization inhibitor, the aqueous adhesive dental composition (X) can have improved storage stability with reduced discoloration and a reduced decrease of adhesive property. The polymerization inhibitor may be phenol-, phosphorus-, sulfur-, or amine-based. Preferred for use is a phenol-based polymerization inhibitor. Specific examples of the polymerization inhibitor include hydroquinone, hydroquinone monomethyl ether, and 2,6-di-t-butyl-4-methylphenol (BHT). Of these, hydroquinone monomethyl ether, and 2,6-di-t-butyl-4-methylphenol are preferred for their strong discoloration and gelation suppressing effect with no inhibitory effect on adhesive property.

The aqueous adhesive dental composition (X) of the present invention may comprise a photopolymerization initiator to impart photocurability. The photopolymerization initiator may be the same photopolymerization initiator used as photopolymerization initiator (f) contained in the curable dental composition (Y) described below. The photopolymerization initiator may be used alone, or two or more thereof may be used in combination.

The aqueous adhesive dental composition (X) may comprise a filler to improve spreadability and flowability. In view of spreadability and flowability, the filler is preferably a fine particle filler having an average particle diameter of 1 nm to 0.1 μm. Specific examples of the filler include Aerosil® OX50, Aerosil® 50, Aerosil® 200, Aerosil® 380, Aerosil® R972, and Aerosil® 130 (products manufactured by Nippon Aerosil Co., Ltd.). The definition of the average particle diameter of the filler contained in the aqueous adhesive dental composition (X), and the method for the measurement of average particle diameter are as defined or described for the filler (g).

The aqueous adhesive dental composition (X) of the present invention may comprise a water-soluble organic solvent to improve bond strength, spreadability, penetrability into tooth structure, and the solubility in water (c) of the radical polymerizable monomer (a) containing an acidic group and the radical polymerizable monomer (d) containing no acidic group. Typically, the water-soluble organic solvent is, for example, a water-soluble organic solvent having a boiling point of 150° C. or less under ordinary pressure, and a solubility of 5 mass % or more for water at 25° C. The water-soluble organic solvent is more preferably one having a solubility of 30 mass % or more for water at 25° C., even more preferably one that can dissolve in water in any proportion. Particularly preferred is a water-soluble organic solvent having a boiling point of 100° C. or less under ordinary pressure. Specific examples of such water-soluble organic solvents include ethanol, methanol, 1-propanol, isopropylalcohol, acetone, methyl ethyl ketone, 1,2-dimethoxyethane, 1,2-diethoxyethane, and tetrahydrofuran. The water-soluble organic solvent may be used alone, or two or more thereof may be used in combination.

In the dental adhesive material kit of the present invention, the aqueous adhesive dental composition (X) is preferably a one-part composition to eliminate the need for mixing, and simplify the procedure.

Curable Dental Composition (Y)

The curable dental composition (Y) is described below.

The curable dental composition (Y) comprises a hydrophilic radical polymerizable monomer (d-1) containing no acidic group, a hydrophobic radical polymerizable monomer (d-2) containing no acidic group, a chemical polymerization initiator (e), a photopolymerization initiator (f), and a filler (g).

Specific examples of the hydrophilic radical polymerizable monomer (d-1) containing no acidic group include the same hydrophilic radical polymerizable monomers used for the aqueous adhesive dental composition (X). The hydrophilic radical polymerizable monomer (d-1) containing no acidic group may be used alone, or two or more thereof may be used in combination.

In view of satisfying both wettability for the aqueous adhesive dental composition (X) and the curability of the curable dental composition (Y), the hydrophilic radical polymerizable monomer (d-1) containing no acidic group contained in the curable dental composition (Y) preferably comprises a bifunctional hydrophilic radical polymerizable monomer (d-1-2) containing no acidic group, more preferably one having a hydroxyl group, particularly preferably 1,2-bis(3-(meth)acryloxy-2-hydroxypropoxy)ethane.

In view of satisfying both the curability and ease of handling of the curable dental composition (Y), the hydrophilic radical polymerizable monomer (d-1) containing no acidic group comprises preferably a monofunctional (meth)acrylamide hydrophilic radical polymerizable monomer containing no acidic group, particularly preferably diethyl (meth)acrylamide.

The content of the hydrophilic radical polymerizable monomer (d-1) containing no acidic group in curable dental composition (Y) is not particularly limited. However, in view of mechanical strength, ease of handling, and adhesive property to tooth structure, the content of the hydrophilic radical polymerizable monomer (d-1) containing no acidic group is preferably 10 to 70 parts by mass, more preferably 20 to 60 parts by mass, even more preferably 30 to 50 parts by mass per 100 parts by mass of the total amount of radical polymerizable monomer (d) containing no acidic group. Here, "total amount of radical polymerizable monomer (d) containing no acidic group" refers to the combined amount of the hydrophilic radical polymerizable monomer (d-1) containing no acidic group and the hydrophobic radical polymerizable monomer (d-2) containing no acidic group in the curable dental composition (Y).

Specific examples of the hydrophobic radical polymerizable monomer (d-2) containing no acidic group include the same hydrophobic radical polymerizable monomers used for the aqueous adhesive dental composition (X) described above. The hydrophobic radical polymerizable monomer (d-2) containing no acidic group may be used alone, or two or more thereof may be used in combination.

In view of obtaining a curable dental composition (Y) having improved mechanical strength, it is preferable that the curable dental composition (Y) comprise a bifunctional hydrophobic radical polymerizable monomer (d-2-2) containing no acidic group, or a trifunctional hydrophobic radical polymerizable monomer (d-2-3) containing no acidic group, particularly preferably N,N'-(2,2,4-trimethylhexamethylene)bis[2-(aminocarboxy)ethan-1-ol]dimethacrylate, 2,2-bis[4-(3-(meth)acryloxy-2-hydroxypropoxy)phenyl]propane, or 2,2-bis(4-(meth)acryloxypolyethoxyphenyl)propane (a compound having an average number of moles of ethoxy group added of 2.6).

The content of the hydrophobic radical polymerizable monomer (d-2) containing no acidic group in curable dental composition (Y) is not particularly limited. However, in view of mechanical strength, the content of hydrophobic radical polymerizable monomer (d-2) containing no acidic group is preferably 30 to 90 parts by mass, more preferably 40 to 80 parts by mass, even more preferably 50 to 70 parts by mass per 100 parts by mass of the total amount of radical polymerizable monomer (d) containing no acidic group.

The curable dental composition (Y) of the present invention may comprise a radical polymerizable monomer (a) containing an acidic group. However, in view of storage stability of the paste, it is preferable that the curable dental composition (Y) of the present invention do not comprise a radical polymerizable monomer (a) containing an acidic group.

In view of further improving adhesive property to tooth structure and dental prosthesis, the curable dental composition (Y) of the present invention comprises a chemical polymerization initiator (e). The chemical polymerization initiator (e) is a component that serves as an oxidizing agent of a redox polymerization initiator.

Examples of the chemical polymerization initiator (e) include organic peroxides, azo compounds, and inorganic peroxides. The chemical polymerization initiator (e) may be used alone, or two or more thereof may be used in combination. Examples of the organic peroxides include diacyl peroxides, peroxy esters, dialkyl peroxides, peroxy ketals, ketone peroxides, and hydroperoxides. Specific examples of the diacyl peroxides include benzoyl peroxide, 2,4-dichlorobenzoyl peroxide, and m-toluoyl peroxide. Specific examples of the peroxy esters include t-butyl peroxybenzoate, bis(t-butylperoxy)isophthalate, 2,5-dimethyl-2,5-bis(benzoylperoxy)hexane, t-butylperoxy-2-ethyl hexanoate, and t-butylperoxy isopropyl carbonate. Specific examples of the dialkyl peroxides include dicumyl peroxide, di-t-butyl peroxide, and lauroyl peroxide. Specific examples of the peroxy ketals include 1,1-bis(t-butylperoxy)3,3,5-trimethylcyclohexane, 1,1-bis(t-butylperoxy)cydohexane, and 1,1-bis(t-hexylperoxy)cyclohexane. Specific examples of the ketone peroxides include methyl ethyl ketone peroxide, cyclohexanone peroxide, and methyl acetoacetate peroxide. Specific examples of the hydroperoxides include t-butyl hydroperoxide, cumene hydroperoxide, p-diisopropylbenzene hydroperoxide, and 1,1,3,3-tetramethylbutyl hydroperoxide. Examples of the azo compounds include 2,2'-azobis(isobutyronitrile), 2,2'-azobis(isobutylnitrile), 2,2'-azobis(4-methoxy-2,4-dimethylvaleronitrile), and 2,2'-azobis(2,4-dimethylvaleronitrile). Examples of the inorganic peroxides include sodium persulfate, potassium persulfate, aluminum persulfate, and ammonium persulfate.

In view of storage stability, preferred among these examples of chemical polymerization initiator (e) are hydroperoxides. Particularly preferred is 1,1,3,3-tetramethylbutyl hydroperoxide for its desirable polymerizability at the interface with a tooth structure.

The content of the chemical polymerization initiator (e) in curable dental composition (Y) is preferably 0.1 to 10 parts by mass relative to 100 parts by mass of the total amount of the radical polymerizable monomer (d) containing no acidic group contained in the curable dental composition (Y). With a chemical polymerization initiator (e) content of less than 0.1 parts by mass, there is a possibility of slowing the cure rate. Accordingly, the content of chemical polymerization initiator (e) is more preferably 0.2 parts by mass or more, even more preferably 0.3 parts by mass or more. With a chemical polymerization initiator (e) content of more than 10 parts by mass, curing may proceed at a rate that is too high to obtain high adhesive property. Accordingly, the content of chemical polymerization initiator (e) is more preferably 7.5 parts by mass or less, even more preferably 5.0 parts by mass or less. For these considerations, the content of chemical polymerization initiator (e) is preferably 0.2 to 7.5 parts by mass, even more preferably 0.3 to 5.0 parts by mass relative to 100 parts by mass of the total mount of the radical polymerizable monomer (d) containing no acidic group contained in the curable dental composition (Y).

Preferably, the curable dental composition (Y) of the present invention does not contain a reducing agent. With a curable dental composition (Y) containing a reducing agent, the storage stability of chemical polymerization initiator (e) and the activity of the polymerization initiator at the interface with a tooth structure may decrease, and this may cause decrease of bond strength.

The photopolymerization initiator (f) in the curable dental composition (Y) of the present invention is essential for imparting photocurability.

Examples of the photopolymerization initiator (f) include (bis)acylphosphine oxides, α-diketones, thioxanthones or quaternary ammonium salts of thioxanthones, ketals, coumarins, anthraquinones, benzoinalkyl ethers, and α-aminoketone compounds. The photopolymerization initiator (f) may be used alone, or two or more thereof may be used in combination. Specific examples of these compounds include the compounds mentioned in WO 2008/087977 A1. Examples of acylphosphine oxides in the (bis)acylphosphine oxides include 2,4,6-trimethylbenzoyldiphenylphosphine oxide, 2,6-dimethoxybenzoykliphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, benzoyl di-(2,6-dimethylphenyl)phosphonate, and salts thereof (for example, sodium salts of 2,4,6-trimethylbenzoylphenylphosphine oxide, potassium salts of 2,4,6-trimethylbenzoyldiphenylphosphine oxide, and ammonium salts of 2,4,6-trimethylbenzoyldiphenylphosphine oxide). Examples of bisacylphosphine oxides include bis(2,6-dichlorobenzoyl)phenylphosphine oxide, bis(2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxybenzoyl)phenylphosphine oxide, bis(2,6-dimethoxybenzoyl)-2,4,4-trimethylpentylphosphine oxide, bis(2,6-dimethoxybenzoyl)-2,5-dimethylphenylphosphine oxide, bis(2,4,6-trimethylbenzoyl)phenylphosphine oxide, bis(2,5,6-trimethylbenzoyl)-2,4,4-trimethylpentylphosphine oxide, and salts thereof. Examples of the α-diketones include diacetyl, benzyl, dl-camphorquinone, 2,3-pentadione, 2,3-octadione, 9,10-phenanthrenequinone, 4,4'-oxybenzyl, and acenaphthenequinone. Particularly preferred is dl-camphorquinone for its maximum absorption wavelength occurring in the visible light region.

The photopolymerization initiator (f) is preferably at least one selected from the group consisting of a (bis)acylphosphine oxide, a salt thereof, and an α-diketone. In this way, a composition can be provided that has desirable photocurability both in the visible light region and the near ultraviolet region so that sufficient photocurability can be ensured regardless of whether the light source used is a halogen lamp, a light emitting diode (LED), or a xenon lamp.

Preferably, the (bis)acylphosphine oxides, α-diketones, thioxanthones or quaternary ammonium salts of thioxanthones, ketals, coumarins, anthraquinones, benzoinalkyl ethers, and α-aminoketone compounds are used with an amine compound to enhance the photopolymerization activity of these compounds, though these compounds show photopolymerization activity themselves. It is preferable to use an amine compound as a polymerization accelerator for the photopolymerization initiator (f), particularly for α-diketones. Examples of the amine compound include methyl 4-(N,N-dimethylamino)benzoate, ethyl 4-(N,N-dimethylamino)benzoate, butyl 4-(N,N-dimethylamino)benzoate, n-butoxyethyl 4-(N,N-dimethylamino)benzoate, lauryl 4-dimethylaminobenzoate, and dimethylaminoethylmethacrylate.

The content of the photopolymerization initiator (f) in the curable dental composition (Y) is not particularly limited. However, in view of photocurability, the content of photopolymerization initiator (f) is preferably 0.01 to 10 parts by mass, more preferably 0.10 to 3.0 parts by mass relative to 100 parts by mass of the total amount of the radical polymerizable monomer (d) containing no acidic group contained in the curable dental composition (Y).

The curable dental composition (Y) of the present invention comprises a filler (g). It is required that the filler (g) be treated with a surface treatment agent comprising a silane coupling agent (A) represented by the general formula [1] above, and an organosilazane (B) represented by the general formula [2] above. With the filler (g) contained in the curable dental composition (Y), the dental adhesive material kit of the present invention exhibits high adhesive property to tooth structure and dental prosthesis even after long storage while maintaining good ease of handling with the paste properties that undergo little change during long storage, and the cured product can exhibit sufficient mechanical strength.

It remains unclear as to why the curable dental composition (Y) of the present invention shows only little change in its paste properties during long storage. However, this can be explained as follows. The surface of filler (g) has a functional group, represented by $-(CH_2)_p-O-(C=O)-C(R^1)=CH_2$ ($R^1$ is a hydrogen atom or a methyl group, and p represents an integer of 1 to 13), derived from a surface treatment with a silane coupling agent (A), and a $C_1$ to $C_3$ alkyl group derived from a surface treatment with an organosilazane (B). The filler (g) has the $-(CH_4-O-(C=O)-C(R^1)=CH_2$ group on its surface. The $-(CH_4-O-(C=O)-C(R^1)=CH_2$ group is imparted by a dehydration polycondensation reaction between silanol groups with a silane coupling agent (A) having a polymerizable group, whereas the $C_1$ to $C_3$ alkyl group is imparted by a deammoniation reaction involving organosilazane (B). In a conventionally known treatment that makes the sole use of silane coupling agent (A), a silanol group ($-SiOH$) yielded by hydrolysis of an alkoxy group of the silane coupling agent (A) and a silanol group ($-SiOH$) on the surface of filler (g) are chemically bonded to each other by dehydration polycondensation. Here, the reaction leaves behind an unreactant, specifically, the silanol group ($-SiOH$) on the surface of filler (g) or the silanol group ($-SiOH$) derived from the silane coupling agent (A) (hereinafter, such a remaining silanol group will be referred to as "remaining silanol group"). In the present invention, however, the remaining silanol group ($-SiOH$) on the surface of filler (g) or the remaining silanol group ($-SiOH$) derived from the silane coupling agent (A) can undergo a deammoniation reaction with the organosilazane (B) and become hydrophobic. Apparently, the treatment (deammoniation reaction) with organosilazane (B) eliminates most, if not all, of the remaining silanol group ($-SiOH$) on the surface of filler (g) or of the remaining silanol group ($-SiOH$) derived from the silane coupling agent (A). This leads to the speculation that the hydroxyl group ($-OH$), ether ($-O-$), and other such groups contained in the hydrophilic radical polymerizable monomer (d-1) containing no acidic group—an essential component for improving wettability for the aqueous adhesive dental composition (X) and adhesive property to tooth structure—become less likely to strongly interact with the silanol group ($-SiOH$) via hydrogen bonding in the curable dental composition (Y), and make the paste properties stable over long storage, posing a significantly low risk of solidification.

This probably explains the little change observed in the paste properties of the curable dental composition (Y) containing the filler (g), even during long storage.

The filler (g) has the —$(CH_2)_p$—O—(C=O)—$C(R^1)$=$CH_2$ group, and the $C_1$ to $C_3$ alkyl group on its surface, as described above. The $C_1$ to $C_3$ alkyl groups are repulsive to each other due to their hydrophobicity. Because of the repulsion between $C_1$ to $C_3$ alkyl groups, the filler (g) of the present invention does not easily aggregate even when used as a component of a dental cement, even in powder form.

The filler (g) may be any known filler commonly used for radical polymerizable curable compositions for dental use, and such fillers can be used without any limitation, as long as the filler is treated with a surface treatment agent and has an average particle diameter of 0.01 to 50.0 μm, and the surface treatment agent comprises the silane coupling agent (A) represented by formula [1], and the organosilazane (B) represented by formula [2]. The filler (g) may be various types of glasses (glasses containing silica as a main component and optionally containing oxides of heavy metals, boron, aluminum, etc.). Examples include glass powders of typical compositions, such as fused silica, quartz, soda lime silica glass, E-glass, C-glass, and borosilicate glass (Pyrex® glass, manufactured by Corning Inc.); and various glass powders for dental use, including, for example, barium glass (GM 27884 and 8235, both manufactured by Schott, and E-2000 and E-3000, both manufactured by Esstech, Inc.), strontium borosilicate glass (E-4000, manufactured by Esstech, Inc.), lanthanum glass ceramic (GM 31684, manufactured by Schott), and fluoroaluminosilicate glass (GM 35429, G018-091, and G018-117, all manufactured by Schott). Other examples of the filler (g) include various types of ceramics, composite oxides (such as silica-titania, and silica-zirconia), diatomaceous earth, kaolin, clay minerals (such as montmorillonite), activated white clay, synthetic zeolite, mica, calcium fluoride, ytterbium fluoride, yttrium fluoride, calcium fluoride of a core-shell structure with a silica-coated surface, ytterbium fluoride of a core-shell structure with a silica-coated surface, yttrium fluoride of a core-shell structure with a silica-coated surface, calcium phosphate, barium sulfate, zirconium dioxide, titanium dioxide, hydroxyapatite, calcium phosphate of a core-shell structure with a silica-coated surface, barium sulfate of a core-shell structure with a silica-coated surface, zirconium dioxide of a core-shell structure with a silica-coated surface, titanium dioxide of a core-shell structure with a silica-coated surface, and hydroxyapatite of a core-shell structure with a silica-coated surface. In view of efficient reaction between filler (g) and silane coupling agent (A) or organosilazane (B), preferred among the foregoing fillers are various types of glasses, composite oxides (such as silica-titania, and silica-zirconia), calcium fluoride of a core-shell structure with a silica-coated surface, ytterbium fluoride of a core-shell structure with a silica-coated surface, yttrium fluoride of a core-shell structure with a silica-coated surface, calcium phosphate of a core-shell structure with a silica-coated surface, barium sulfate of a core-shell structure with a silica-coated surface, zirconium dioxide of a core-shell structure with a silica-coated surface, titanium dioxide of a core-shell structure with a silica-coated surface, and hydroxyapatite of a core-shell structure with a silica-coated surface. These may be used alone, or two or more thereof may be used in combination.

The average particle diameter of the filler (g) is 0.01 to 50.0 μm, preferably 0.03 to 20.0 μm, more preferably 0.05 to 10.0 μm. With the average particle diameter of filler (g) falling in these ranges, a sufficient mechanical strength can be obtained, and the paste does not develop stickiness, which is problematic for ease of handling. With the foregoing average particle diameter ranges, it is also possible to improve the gloss polishability and gloss durability of the cured product. In the present specification, the average particle diameter of filler means the average particle diameter of primary particles of the filler (average primary particle diameter).

The average particle diameter of filler can be determined by particle size distribution analysis or electron microscopy. The use of a particle size distribution analyzer is preferred for particles with an average particle diameter of 1.0 μm or more, whereas electron microscopy is preferred for particles with an average particle diameter of less than 1.0 μm. As a specific example of particle size distribution measurement, a laser diffraction particle size distribution analyzer (SALD-2300, manufactured by Shimadzu Corporation) may be used with a 0.2% sodium hexametaphosphate aqueous solution used as dispersion medium. As a specific example of electron microscopy, particles may be photographed with a scanning electron microscope (Model S-4000, manufactured by Hitachi), and the size of particles (at least 200 particles) observed in a unit field of the micrograph may be measured using image-analyzing particle-size-distribution measurement software (Macview; Mountech Co., Ltd.). Here, the particle diameter is determined as an arithmetic mean value of the maximum and minimum lengths of particles, and the average primary particle diameter is calculated from the number of particles and the particle diameter.

The filler (g) does not easily aggregate, and can be easily washed with water.

This makes it possible to reduce the content of ionic impurities, such as an alkali metal, which undergo an acid-base reaction or chelation reaction with the radical polymerizable monomer (a) containing an acidic group.

The filler (g) can be obtained by surface treatment with the silane coupling agent (A) represented by formula [1] and the organosilazane (B) represented by formula [2].

The surface treatment with the silane coupling agent (A) represented by formula [1] replaces the hydroxy group present on the surface of filler (g) with a functional group derived from the silane coupling agent (A).

The order of the surface treatment of the filler (g) is not particularly limited.

For example, the silane coupling agent (A) represented by formula [1] and the organosilazane (B) represented by formula [2] may be added sequentially or simultaneously for the surface treatment of the filler (g). As an example, the filler (g) may be reacted first with the silane coupling agent (A) represented by formula [1], and then with the organosilazane (B) represented by formula [2]. Alternatively, the filler (g) may be reacted first with the organosilazane (B) represented by formula [2], and then with the silane coupling agent (A) represented by formula [1], and again with the organosilazane (B) represented by formula [2].

The method for the surface treatment of the filler (g) is not particularly limited, as long as the method binds the silane coupling agent (A) represented by formula [1] to the surface of the filler (g) by dehydration polycondensation reaction, and binds the organosilazane (B) represented by formula [2] to the surface of the filler (g) by deammoniation reaction. The method for the surface treatment of filler (g) may be, for example, a method that heats and dries the filler (g) for a certain time period while stirring the filler (g) in a mixing chamber after spraying a dilute solution of each surface treatment agent over the filler (g) being stirred in the mixing chamber, or a method that heats and dries the filler (g) after stirring and mixing the filler (g) with the surface treatment agents in a solvent. Examples of the solvent include, but are not particularly limited to, alcohol solvents such as methanol, ethanol, and isopropanol, water, and a mixed solvent thereof. The heating temperature is not particularly limited, and may be about 30 to 90° C.

In formula [1], $R^1$ is a hydrogen atom or a methyl group. $R^2$ is an optionally substituted hydrolyzable group. $R^3$ is an optionally substituted $C_1$ to $C_3$ alkyl group. The symbol p is an integer of 1 to 13, preferably 2 to 10, more preferably 2 to 8, even more preferably 2 to 6. The symbol q is 2 or 3, preferably 3.

The optionally substituted hydrolyzable group represented by $R^2$ is not particularly limited. Examples of the hydrolyzable group include linear or branched $C_1$ to $C_6$ alkoxy groups (such as methoxy, ethoxy, n-propoxy, isopropoxy, n-butoxy, sec-butoxy, isobutoxy, tert-butoxy, pentyloxy, isopentyloxy, hexyloxy, and isohexyloxy), a chlorine atom, and an isocyanate group. Considering hydrolyzability, the alkoxy group as a hydrolyzable group is more preferably a linear $C_1$ to $C_4$ alkoxy group selected from methoxy, ethoxy, n-propoxy, and n-butoxy, even more preferably a linear $C_1$ to $C_3$ alkoxy group. $R^2$ may be an unsubstituted hydrolyzable group, or an unsubstituted linear or branched $C_1$ to $C_6$ alkoxy group. $R^3$ may be an unsubstituted $C_1$ to $C_3$ alkyl group. The silane coupling agent (A) represented by formula [1] is preferably one in which $R^1$ is a methyl group, $R^2$ is an unsubstituted linear or branched $C_1$ to $C_3$ alkoxy group, $R^3$ is an unsubstituted $C_1$ to $C_3$ alkyl group, p is 2 to 10, and q is 2 or 3, more preferably one in which $R^1$ is a methyl group, $R^2$ is an unsubstituted linear or branched $C_1$ to $C_4$ alkoxy group, p is 2 to 8, and q is 3, even more preferably one in which $R^1$ is a methyl group, $R^2$ is an unsubstituted linear or branched $C_1$ to $C_3$ alkoxy group, p is 2 to 6, and q is 3.

Examples of the optionally substituted $C_1$ to $C_3$ alkyl group represented by $R^3$, $R^4$, $R^5$, $R^6$, $R^7$, $R^8$, and $R^9$ include methyl, ethyl, n-propyl, and isopropyl. $R^4$, $R^5$, $R^6$, $R^7$, $R^8$, and $R^9$ may each independently represent an unsubstituted $C_1$ to $C_3$ alkyl group. At least one of $R^4$, $R^5$, and $R^6$ may be an unsubstituted $C_1$ to $C_3$ alkyl group, and at least one of $R^7$, $R^8$, and $R^9$ may be an unsubstituted $C_1$ to $C_3$ alkyl group. The alkyl group represented by $R^4$, $R^5$, $R^6$, $R^7$, $R^8$, and $R^9$ is preferably a methyl group or an ethyl group, more preferably a methyl group. At least one of $R^4$, $R^5$, and $R^6$ may be an optionally substituted $C_1$ to $C_3$ alkyl group, two of $R^4$, $R^5$, and $R^6$ may be optionally substituted $C_1$ to $C_3$ alkyl groups, and all three of $R^4$, $R^5$, and $R^6$ may be optionally substituted $C_1$ to $C_3$ alkyl groups. At least one of $R^7$, $R^8$, and $R^9$ may be an optionally substituted $C_1$ to $C_3$ alkyl group, two of $R^7$, $R^8$, and $R^9$ may be optionally substituted $C_1$ to $C_3$ alkyl groups, and all three of $R^7$, $R^8$, and $R^9$ may be optionally substituted $C_1$ to $C_3$ alkyl groups.

Examples of the substituent in the hydrolyzable group represented by $R^2$, and examples of the substituent in the alkyl group represented by $R^3$, $R^4$, $R^5$, $R^6$, $R^7$, $R^8$, and $R^9$ include a halogen atom (a fluorine, chlorine, bromine, or iodine atom), a carboxy group, a hydroxy group, an amino group, an amino group mono- or di-substituted with a $C_1$ to $C_6$ alkyl group, an acyl group, and a $C_1$ to $C_6$ alkyl group. The number of substituents is not particularly limited. For example, the number of substituents in the hydrolyzable group represented by $R^2$ is 1 to 5, and the number of substituents in the alkyl group represented by $R^3$, $R^4$, $R^5$, $R^6$, $R^7$, $R^8$ and $R^9$ is 1, 2, or 3.

Specific examples of the silane coupling agent (A) represented by formula [1] include (meth)acryloxymethyltrimethoxysilane, 2-(meth)acryloxyethyltrimethoxysilane, 3-(meth)acryloxypropyltrimethoxysilane, 4-(meth)acryloxybutyltrimethoxysilane, 5-(meth)acryloxypentyltrimethoxysilane, 6-(meth)acryloxyhexyltrimethoxysilane, 7-(meth)acryloxyheptyltrimethoxysilane, 8-(meth)acryloxyoctyltrimethoxysilane, 9-(meth)acryloxynonyltrimethoxysilane, 10-(meth)acryloxydecyltrimethoxysilane, 11-(meth)acryloxyundecyltrimethoxysilane, 11-(meth)acryloxyundecyldichloromethylsilane, 11-(meth)acryloxyundecyltrichlorosilane, 11-(meth)acryloxyundecyldimethoxymethylsilane, 12-(meth)acryloxydodecyltrimethoxysilane, and 13-(meth)acryloxytridecyltrimethoxysilane. The silane coupling agent (A) may be used alone, or two or more thereof may be used in combination as appropriate. Among these compounds, 2-(meth)acryloxyethyltrimethoxysilane, 3-(meth)acryloxypropyltrimethoxysilane, 4-(meth)acryloxybutyltrimethoxysilane, 5-(meth)acryloxypentyltrimethoxysilane, and 6-(meth)acryloxyhexyltrimethoxysilane are preferred, and 3-(meth)acryloxypropyltrimethoxysilane is more preferred because the alkylene group represented by $—(CH_2)_p—$, when moderately long, can improve the compatibility with the polymerizable monomers contained in the curable dental composition (Y), and ensure a sufficiently high content for the filler (g) contained in the curable dental composition (Y), and, when moderately short, increases the bond strength by preventing the silane coupling agent (A) from turning overly hydrophobic.

The organosilazane (B) is a compound that undergoes a deammoniation reaction to bind to the hydroxy group present on the surface of the filler (g), and to the hydroxy group derived from the silane coupling agent (A). Preferably, the organosilazane (B) is a compound having a small molecular weight. Specific examples of the organosilazane (B) include hexaethyldisilazane, hexa-n-propyldisilazane, hexaisopropyldisilazane, 1,1,2,2-tetramethyl-3,3-diethyldisilazane, 1,1,3,3-tetramethyldisilazane, 1,1,1,3,3,3-hexamethyldisilazane, and 1,1,1,3,3-pentamethyldisilazane. Preferred are, for example, 1,1,3,3-tetramethyldisilazane, 1,1,1,3,3,3-hexamethyldisilazane, and 1,1,1,3,3-pentamethyldisilazane. The organosilazane (B) may be used alone, or two or more thereof may be used in combination as appropriate.

The filler (g) is treated with preferably 0.5 to 15 parts by mass, more preferably 1 to 10 parts by mass, particularly preferably 2 to 8 parts by mass of silane coupling agent (A) relative to 100 parts by mass of the filler (g) to be treated. A surface treatment with less than 0.5 parts by mass of silane coupling agent (A) may result in the failure to sufficiently impart the polymerizable group to the surface of the filler (g), and the mechanical strength may decrease.

In the surface treatment of the filler (g), the mole ratio of silane coupling agent (A) to organosilazane (B) is preferably 1:1 to 1:20, more preferably 1:2 to 1:10. When the fraction of organosilazane (B) is smaller than the fraction of silane coupling agent (A), there is a possibility of progression of aggregation in the paste, and it may not be possible to ensure transparency during storage. When the amount of organosilazane (B) is more than 20 mol per mole of silane coupling agent (A), the hydrophobicity may increase, and it may not be possible to obtain a sufficient bond strength.

In the surface treatment process, a polymerization inhibitor may be added to inhibit the polymerization of the silane coupling agent (A). The polymerization inhibitor may be a known polymerization inhibitor such as 2,6-di-t-butyl-4-methylphenol (BHT) or p-methoxyphenol (methoquinone).

It is preferable that the surface treatment agent used in the surface treatment of the filler (g) consist essentially of the silane coupling agent (A) represented by formula [1] and the organosilazane (B) represented by formula [2]. By "consisting essentially of silane coupling agent (A) and organosilazane (B)" it means that the content of a surface treatment agent or agents other than silane coupling agent (A) and organosilazane (B) is less than 1.0 mass %. The content of a surface treatment agent or agents other than silane coupling agent (A) and organosilazane (B) is preferably less than 0.5 mass %, more preferably less than 0.1 mass %.

The filler (g) is preferably one that is solidified after the surface treatment. The solidification of filler (g) is a process in which the filler (g) having undergone a surface treatment is precipitated with a mineral acid, and the precipitate is washed with water and/or dehydrated (e.g., dried) to obtain a solid of filler (g). As described above, an ordinary filler surface-treated with the silane coupling agent (A) alone aggregates very easily, and it is very difficult to redisperse such a filler once it is solidified. However, because the filler (g) of the present invention does not easily aggregate, aggregation does not easily take place even after solidification, and the filler (g) can be redispersed with ease even if it aggregates. As described above, the filler (g) containing a small amount of ionic impurities such as alkali metals can be easily produced by washing the filler (g) with water. The use of the filler (g) containing a small amount of ionic impurities makes it possible to further reduce a possible interaction between ionic impurities and the very small amount of remaining silanol groups, and further inhibit changes in paste properties, including transparency. In the washing process, washing is preferably repeated until the electrical conductivity of the extract water (for example, water after immersion of the filler (g) at 121° C. for 24 hours) of the filler (g) reaches 50 µS/cm or less.

Examples of the mineral acid used for solidification include inorganic acids such as hydrochloric acid, nitric acid, sulfuric acid, and phosphoric acid. Hydrochloric acid is particularly preferred. The mineral acid may be used as it is, and is preferably used in the form of an aqueous solution. The concentration of the mineral acid in the aqueous solution is preferably 0.1 mass % or more, more preferably 0.5 mass % or more. The amount of the aqueous solution of mineral acid may be about 6 to 12 times greater than the mass of the filler (g) to be washed.

Washing with an aqueous solution of mineral acid may be performed multiple times. In washing with an aqueous solution of mineral acid, the filler (g) is preferably stirred after being immersed in an aqueous solution of mineral acid. The filler (g) immersed in the aqueous solution may be left unattended for 1 to 24 hours, or even as long as about 72 hours. The filler (g) may be left unattended with or without stirring. Washing in a solution of mineral acid may involve heating to an ordinary temperature or higher temperatures. The filler (g) is collected by filtration, and washed with water. Preferably, the water used for washing does not contain ions, for example, alkali metal ions (1 ppm or less by mass). Examples of such water include ion-exchange water, distilled water, and purified water. In washing with water, the filler (g) may be filtered after being dispersed or suspended, as with the case of washing with an aqueous solution of mineral acid, or water may be continuously passed through the filler (g) after filtration. The end point of washing with water may be determined by the electrical conductivity of the extract water. Alternatively, the end point of washing with water may be when the concentration of alkali metals in the discharged water from washing of the filler (g) has reached 1 ppm or less, or when the concentration of alkali metals in extract water has reached 5 ppm or less. Washing with water may involve heating to an ordinary temperature or higher temperatures.

The filler (g) can be dried using an ordinary method. For example, the filler (g) may be heated, or may be left unattended under reduced pressure (vacuum). The heater and decompressor used for this purpose are not particularly limited, and known apparatuses can be used.

Other than drying, the filler (g) may be dehydrated by adding an aqueous organic solvent having a higher boiling point than water to the filler (g) containing water, and removing water by mixing a material that is soluble in the aqueous organic solvent. Examples of the aqueous organic solvent include propylene glycol monomethyl ether (propylene glycol-1-methyl ether having a boiling point of about 119° C.; propylene glycol-2-methyl ether having a boiling point of about 130° C.), butanol (having a boiling point of 117.7° C.), N-methyl-2-pyrrolidone (having a boiling point of about 204° C.), γ-butyrolactone (having a boiling point of about 204° C.).

The content of the filler (g) in curable dental composition (Y) is not particularly limited. However, in view of mechanical strength and ease of handling, the content of the filler (g) in curable dental composition (Y) is preferably 50 to 500 parts by mass, more preferably 75 to 400 parts by mass, even more preferably 100 to 300 parts by mass relative to 100 parts by mass of the total amount of the radical polymerizable monomer (d) containing no acidic group contained in curable dental composition (Y).

The curable dental composition (Y) of the present invention may comprise a filler (h) that does not use organosilazane (B) as a surface treatment agent, as long as use of such a filler does not cause changes in paste properties or pose a solidification risk during long storage. The filler (h) is a component intended to impart X-ray opacity to the dental cement, or to add strength to the matrix or improve the ease of handling of the paste. The term "X-ray opacity" as used in the present specification refers to the performance of a solidified dental material to distinguish itself from the tooth structure in an examination with a dental X-ray apparatus commonly used in conventional methods. A dental material having X-ray opacity is advantageous in specific situations where tooth conditions are diagnosed using X-rays.

The filler (h) may be any known filler commonly used for radical polymerizable curable compositions for dental use, and such fillers may be used without any limitation, except for those prepared by flame hydrolysis. The filler (h) may be various types of glasses (glasses containing silica as a main component and optionally containing oxides of heavy metals, boron, aluminum, etc.). Examples include glass powders of typical compositions, such as fused silica, quartz, soda lime silica glass, E-glass, C-glass, and borosilicate glass (Pyrex® glass, manufactured by Corning Inc.); and various glass powders for dental use, including, for example, strontium borosilicate glass (E-4000, manufactured by Esstech, Inc.), lanthanum glass ceramic (GM 31684, manufactured by Schott), and fluoroaluminosilicate glass (GM 35429, G018-091, and G018-117, all manufactured by Schott). Other examples of the filler (h) include various types of ceramics, composite oxides (such as silica-titania, and silica-zirconia), diatomaceous earth, kaolin, clay minerals (such as montmorillonite), activated white clay, synthetic zeolite, mica, calcium fluoride, ytterbium fluoride, yttrium fluoride, calcium fluoride of a core-shell structure with a silica-coated surface, ytterbium fluoride of a core-shell structure with a silica-coated surface, yttrium fluoride of a core-shell structure with a silica-coated surface, calcium phosphate, barium sulfate, zirconium dioxide, titanium dioxide, hydroxyapatite, calcium phosphate of a core-shell structure with a silica-coated surface, barium sulfate of a core-shell structure with a silica-coated surface, zirconium dioxide of a core-shell structure with a silica-coated surface, titanium dioxide of a core-shell structure with a silica-coated surface, and hydroxyapatite of a core-shell structure with a silica-coated surface. Individually, these may be used alone, or two or more thereof may be used in combination. In view of the ability to exhibit X-ray opacity in small amounts, and allowing for a treatment with the silane coupling agent (A), preferred are ytterbium fluoride of a core-shell structure with a silica-coated surface, and yttrium fluoride of a core-shell structure with a silica-coated surface. It is not preferable to add a filler prepared by flame hydrolysis because, in that case, the paste becomes notably thixotropic by the presence of the hydroxyl or other groups on the filler surface having a large specific surface area, and shows greatly different paste properties immediately after preparation and after storage. Examples of commercially available fillers prepared by flame hydrolysis include Aerosil®, Aeroxide® AluC, Aeroxide® $TiO_2$ P25, VP Zirconium Oxide 3-YSZ, and VP Zirconium Oxide 3-YSZ PH, manufactured by Nippon Aerosil Co., Ltd.

The average particle diameter of the filler (h) is preferably 0.01 to 50.0 μm, more preferably 0.05 to 20.0 μm, even more preferably 0.08 to 10.0 μm, particularly preferably 0.10 to 4.50 μm. With the average particle diameter of filler (h) falling in these ranges, a sufficient mechanical strength can be obtained, and the paste does not develop stickiness, which is problematic for ease of handling. With the foregoing average particle diameter ranges, it is also possible to improve the gloss polishability and gloss durability of the cured product. The definition of the average particle diameter of filler (h), and the method for the measurement of average particle diameter are as defined or described for the filler (g).

Preferably, the filler (h) is surface-treated in advance with a surface treatment agent that does not contain organosilazane (B) so that the filler (h) can have improved affinity for the polymerizable monomer components in curable dental composition (Y), and can improve the mechanical strength of the cured product by forming stronger chemical bonds with the polymerizable monomer components.

Examples of such a surface treatment agent include at least one organometallic compound selected from the group consisting of an organosilicon compound, an organotitanium compound, an organozirconium compound, and an organoaluminum compound. When two or more organometallic compounds are used, the organometallic compounds may form a surface treatment layer as a mixture of two or more organometallic compounds, or a surface treatment layer of a multilayer structure formed as a laminate of two or more organometallic compound layers.

Examples of the organosilicon compound include compounds represented by $(R^{10})_n SiY_{4-n}$, wherein $R^{10}$ is a substituted or unsubstituted $C_1$ to $C_{12}$ hydrocarbon group, Y is a $C_1$ to $R^4$ alkoxy group, a hydroxyl group, a halogen atom, or a hydrogen atom, and n is 0, 1, 2, or 3, in which $R^{10}$ may be the same or different when a plurality of $R^{10}$ exists, and Y may be the same or different when a plurality of Y exists.

Specific examples of the organosilicon compound include methyltrimethoxysilane, dimethyldimethoxysilane, phenyltrimethoxysilane, diphenyldimethoxysilane, methyltriethoxysilane, dimethyldiethoxysilane, phenyltriethoxysilane, diphenyldiethoxysilane, isobutyltrimethoxysilane, vinyltrimethoxysilane, vinyltriethoxysilane, vinyltris(β-methoxyethoxy)silane, 3,3,3-trifluoropropyltrimethoxysilane, methyl(3,3,3-trifluoropropyl)dimethoxysilane, β-(3,4-epoxycyclohexyl)ethyltrimethoxysilane, γ-glycidoxypropyltrimethoxysilane, γ-glycidoxypropylmethyldiethoxysilane, γ-glycidoxypropyltriethoxysilane, γ-methacryloxypropylmethyldimethoxysilane, γ-methacryloxypropylmethyldiethoxysilane, N-(β-aminoethyl)-γ-aminopropylmethyldimethoxysilane, N-(β-aminoethyl)-γ-aminopropyltrimethoxysilane, N-(β-aminoethyl)-γ-aminopropyltriethoxysilane, γ-aminopropyltrimethoxysilane, γ-aminopropyltriethoxysilane, N-phenyl-γ-aminopropyltrimethoxysilane, γ-mercaptopropyltrimethoxysilane, trimethylsilanol, methyltrichlorosilane, methyldichlorosilane, dimethyldichlorosilane, trimethylchlorosilane, phenyltrichlorosilane, diphenyldichlorosilane, vinyltrichlorosilane, trimethylbromosilane, diethylsilane, vinyltriacetoxysilane, ω-(meth)acryloxyalkyltrimethoxysilane (having 3 to 12 carbon atoms between the (meth)acryloxy group and the silicon atom; e.g., γ-methacryloxypropyltrimethoxysilane), and ω-(meth)acryloxyalkyltriethoxysilane (having 3 to 12 carbon atoms between the (meth)acryloxy group and the silicon atom; e.g., γ-methacryloxypropyltriethoxysilane).

Particularly preferred among these compounds are coupling agents having a functional group copolymerizable with the above polymerizable monomer components. Examples of such coupling agents include ω-(meth)acryloxyalkyltrimethoxysilane (having 3 to 12 carbon atoms between the (meth)acryloxy group and the silicon atom), ω-(meth)acryloxyalkyltriethoxysilane (having 3 to 12 carbon atoms between the (meth)acryloxy group and the silicon atom), vinyltrimethoxysilane, vinyltriethoxysilane, vinyltriacetoxysilane, and γ-glycidoxypropyltrimethoxysilane.

Examples of the organotitanium compound include tetramethyl titanate, tetraisopropyl titanate, tetra-n-butyl titanate, butyl titanate dimer, and tetra(2-ethylhexyl) titanate.

Examples of the organozirconium compound include zirconium isopropoxide, zirconium n-butoxide, zirconium acetylacetonate, and zirconyl acetate.

Examples of the organoaluminum compound include aluminum acetylacetonate, and a chelate compound of a salt of aluminum and organic acid.

The shape of the filler (h) is not particularly limited. The shape of the filler (h) may be selected as appropriate depending on the properties that need to be improved for the dental cement. Specifically, the filler (h) may be used in the form of a powder of irregular-shaped or spherical particles. An irregular-shaped filler (h) is particularly desirable for improving mechanical strength and wear resistance. A spherical filler (h) is particularly desirable for improving gloss polishability and gloss durability. A commercially available filler may be used as the filler (h) of the present invention.

The content of filler (h) is not particularly limited, as long as the effects of the present invention can be obtained. The content of filler (h) is in the range of preferably 1 to 200 parts by mass, more preferably 10 to 150 parts by mass, particularly preferably 30 to 100 parts by mass relative to 100 parts by mass of the total amount of the radical polymerizable monomer (d) containing no acidic group in curable dental composition (Y). With the filler (h) content falling in these ranges, the cured product can have sufficient X-ray opacity or sufficient mechanical strength while ensuring sufficient ease of handling for the paste.

The curable dental composition (Y) of the present invention may be a two-pack composition or a one-pack composition. Preferably, the curable dental composition (Y) of the present invention is a one-pack composition.

Optional Components

The optional components of a dental adhesive material kit of the present invention are described below. Typically, the optional components are contained in at least one of the aqueous adhesive dental composition (X) and the curable dental composition (Y). However, a dental adhesive material kit of the present invention may be a kit comprising materials other than the aqueous adhesive dental composition (X) and the curable dental composition (Y), and the optional components may be contained in such materials.

The dental adhesive material kit of the present invention may further comprise a fluorine-ion releasing material. For example, with a fluorine-ion releasing material added to the curable dental composition (Y), a curable dental composition can be obtained that imparts acid resistance to a tooth structure. Examples of the fluorine ion-releasing material include metal fluorides such as sodium fluoride, potassium fluoride, sodium monofluorophosphate, lithium fluoride, and ytterbium fluoride. The fluorine ion-releasing material may be used alone, or two or more thereof may be used in combination.

The dental adhesive material kit of the present invention may also comprise other optional components, for example, such as a pH adjuster, a polymerization inhibitor, an ultraviolet absorber, a thickener, a colorant, an antibacterial agent, and a flavor, as long as the addition of these optional components does not interfere with the effects of the present invention.

In all of the embodiments described above, the type and content of each component in the aqueous adhesive dental composition (X) and curable dental composition (Y), and other conditions of the components in these compositions may be appropriately selected or varied within the ranges specified in different parts of the specification.

A preferred embodiment (Z-1) of the present invention is, for example, a dental adhesive material kit comprising an aqueous adhesive dental composition (X) and a curable dental composition (Y), wherein the curable dental composition (Y) comprises 50 to 500 parts by mass of a filler (g) relative to 100 parts by mass of the total amount of a radical polymerizable monomer (d) containing no acidic group, 10 to 70 parts by mass of a hydrophilic radical polymerizable monomer (d-1) containing no acidic group per 100 parts by mass of the total amount of the radical polymerizable monomer (d) containing no acidic group, and 30 to 90 parts by mass of a hydrophobic radical polymerizable monomer (d-2) containing no acidic group per 100 parts by mass of the total amount of the radical polymerizable monomer (d) containing no acidic group. Another preferred embodiment (Z-2) is, for example, a dental adhesive material kit comprising an aqueous adhesive dental composition (X) and a curable dental composition (Y), wherein the curable dental composition (Y) comprises 75 to 400 parts by mass of a filler (g) relative to 100 parts by mass of the total amount of a radical polymerizable monomer (d) containing no acidic group, 20 to 60 parts by mass of a hydrophilic radical polymerizable monomer (d-1) containing no acidic group per 100 parts by mass of the total amount of the radical polymerizable monomer (d) containing no acidic group, and 40 to 80 parts by mass of a hydrophobic radical polymerizable monomer (d-2) containing no acidic group per 100 parts by mass of the total amount of the radical polymerizable monomer (d) containing no acidic group. Another preferred embodiment (Z-3) is, for example, a dental adhesive material kit comprising an aqueous adhesive dental composition (X) and a curable dental composition (Y), wherein the curable dental composition (Y) comprises 100 to 300 parts by mass of a filler (g) relative to 100 parts by mass of the total amount of a radical polymerizable monomer (d) containing no acidic group, 30 to 50 parts by mass of a hydrophilic radical polymerizable monomer (d-1) containing no acidic group per 100 parts by mass of the total amount of the radical polymerizable monomer (d) containing no acidic group, and 50 to 70 parts by mass of a hydrophobic radical polymerizable monomer (d-2) containing no acidic group per 100 parts by mass of the total amount of the radical polymerizable monomer (d) containing no acidic group. Preferably, in the preferred embodiments (Z-1), (Z-2), and (Z-3), the dental adhesive material kit is one in which the aqueous adhesive dental composition (X) comprises 1 to 45 parts by mass of a radical polymerizable monomer (a) containing an acidic group, 5 to 74 parts by mass of water (c), and 25 to 70 parts by mass of a radical polymerizable monomer (d) containing no acidic group per 100 parts by mass of the total amount of radical polymerizable monomers and solvent, and 0.0001 parts by mass to 10 parts by mass of a polymerization accelerator (b) relative to 100 parts by mass of the total amount of the radical polymerizable monomers. More preferably, in the preferred embodiments (Z-1), (Z-2), and (Z-3), the dental adhesive material kit is one in which the aqueous adhesive dental composition (X) comprises 5 to 40 parts by mass of a radical polymerizable monomer (a) containing an acidic group, 10 to 60 parts by mass of water (c), and 28 to 60 parts by mass of a radical polymerizable monomer (d) containing no acidic group per 100 parts by mass of the total amount of radical polymerizable monomers and solvent, and 0.0005 parts by mass to 5.0 parts by mass of a polymerization accelerator (b) relative to 100 parts by mass of the total amount of the radical polymerizable monomers. Even more preferably, in the preferred embodiments (Z-1), (Z-2), and (Z-3), the dental adhesive material kit is one in which the aqueous adhesive dental composition (X) comprises 10 to 38 parts by mass of a radical polymerizable monomer (a) containing an acidic group, 15 to 45 parts by mass of water (c), and 30 to 55 parts by mass of a radical polymerizable monomer (d) containing no acidic group per 100 parts by mass of the total amount of radical polymerizable monomers and solvent, and 0.001 parts by mass to 1.0 part by mass of a polymerization accelerator (b) relative to 100 parts by mass of the total amount of the radical polymerizable monomers.

A dental adhesive material kit of the present invention exhibits high adhesive property to tooth structure and dental prosthesis through photopolymerization while ensuring desirable storage stability and good ease of handling with the paste properties that undergo little change during long storage. In a dental adhesive material kit of the present invention, a cured product of the curable dental composition (Y) has desirable mechanical strength. In a dental adhesive material kit of the present invention, the curable dental composition (Y) has desirable stringiness. This makes a dental adhesive material kit of the present invention preferred for use as a dental cement kit, for example, a dental veneer cement kit used to apply a veneer cement to the inner surface (bonding surface) of a veneer with a syringe. A dental adhesive material kit of the present invention is a photopolymerizable dental adhesive material kit containing a photopolymerization initiator (f), and shows high adhesive property to tooth structure and dental prosthesis with enough time afforded for the procedure, and the cured product has high mechanical strength. This makes a dental adhesive material kit of the present invention suited for veneer treatment, and preferred for use as a dental veneer cement kit.

EXAMPLES

The following describes the present invention by way of Examples and Comparative Examples. It should be noted that the present invention is in no way limited by the following descriptions. The abbreviations used in Examples and Comparative Examples are as follows.
Radical Polymerizable Monomer (a) Containing an Acidic Group
    MDP: 10-Methacryloxydecyl dihydrogen phosphate
Polymerization Accelerator (b)
    VOAA: Vanadyl(IV) acetylacetonate
    BMOV: Bis(maltolato)oxovanadium(IV)
Water (c)
    Water: Purified water
Hydrophilic Radical Polymerizable Monomer (d-1) Containing no Acidic Group
    HEMA: 2-Hydroxyethylmethacrylate
    #801: 1,2-Bis(3-methacryloxy-2-hydroxypropoxy)ethane
    3G: Triethylene glycol dimethacrylate
    DEAA: Diethylacrylamide
    DMAA: Dimethylacrylamide
Hydrophobic Radical Polymerizable Monomer (d-2) Containing no Acidic Group
    Bis-GMA: 2,2-Bis[4-(3-methacryloxy-2-hydroxypropoxy)phenyl]propane
    D2.6E: 2,2-Bis(4-methacryloxypolyethoxyphenyl)propane (a compound having an average number of moles of ethoxy group added of 2.6)
    UDMA: N,N'-(2,2,4-Trimethylhexamethylene)bis[2-(aminocarboxy)ethan-1-ol]dimethacrylate
Chemical Polymerization Initiator (e)
    THP: 1,1,3,3-Tetramethylbutylhydroperoxide
    CHP: Cumene hydroperoxide
    BPO: Benzoyl peroxide
Photopolymerization Initiator (f)
    CQ: dl-Camphorquinone
Polymerization Inhibitor
    BHT: 2,6-di-t-Butyl-4-methylphenol
Other
    JJA: 4-(N, N-Dimethylamino)ethyl benzoate
    Filler (g)
TMS-SiO$_2$—1: Filler (g-1)

Production Example 1

Production of Filler (g-1)

A Snowtex OL—a type of colloidal silica manufactured by Nissan Chemical Industries, Ltd., available in the form of an aqueous dispersion of 20% silica particles having an average particle diameter of 50 nm—was prepared as silica particles. Isopropanol was prepared as alcohol. 3-Methacryloxypropyltrimethoxysilane (KBM-503, manufactured by Shin-Etsu Chemical Co., Ltd.) was prepared as silane coupling agent (A). 1,1,1,3,3,3-Hexamethyldisilazane (HMDS; HMDS-1 manufactured by Shin-Etsu Chemical Co., Ltd.) was prepared as organosilazane (B). An amount of 60 parts by mass of isopropanol was added to 100 parts by mass of a slurry prepared as a 20 mass % aqueous dispersion of the silica particles. These were then mixed at room temperature (25° C.) to obtain a dispersion containing the silica particles dispersed in liquid medium. To the dispersion were added 0.48 parts by mass of 3-methacryloxypropyltrimethoxysilane and 0.01 parts by mass of a polymerization inhibitor (2,6-di-t-butyl-4-methylphenol (BHT), manufactured by Kanto Kagaku), and these were mixed at 40° C. for 72 hours. This is a surface treatment process that treats the hydroxyl groups present on silica particle surfaces with the silane coupling agent (A). It is to be noted here that 3-methacryloxypropyltrimethoxysilane was added in the foregoing amount to ensure that the hydroxyl groups on silica particles (some of the hydroxyl groups) remain untreated. The mixture was left unattended at 40° C. for 72 hours after adding 0.78 parts by mass of 1,1,1,3,3,3-hexamethyldisilazane. This produced a silica particle material through the surface treatment of the silica particles. The silica particles, by turning hydrophobic in the course of surface treatment, became unable to stably exist in water and isopropanol, and precipitated by forming aggregates. In the surface treatment agent, 3-methacryloxypropyltrimethoxysilane and hexamethyldisilazane had a mole ratio of 2:5. After the surface treatment, 2.6 parts by mass of a 35% hydrochloric acid aqueous solution was added to the total amount of the mixture to precipitate the silica particle material. The precipitate was collected by filtration using a filter paper (No. 5A, manufactured by Advantec Co., Ltd.). The filtration residue (solids) was then washed with purified water, and vacuum dried at 100° C. to obtain a filler (g-1) having an average particle diameter of 50 nm.

TMS-SiO$_2$—2: Filler (g-2)

Production Example 2

Production of Filler (g-2)

A filler (g-2) (average particle diameter 50 nm) was produced in the same manner as in the production of the filler (g-1) in Production Example 1, except that 2.8 parts by mass of 1,1,1,3,3,3-hexamethyldisilazane was used. In the surface treatment agent, 3-methacryloxypropyltrimethoxysilane and hexamethyldisilazane had a mole ratio of 2:18.
Filler (h)
Surface-Treated Silica: Silane-Treated Silica Stone Powder
A silica stone powder (Hi-Silica, manufactured by Nitchitsu Co., Ltd.) was pulverized with a ball mill to obtain a pulverized silica stone powder. The pulverized silica stone powder had an average particle diameter of 2.2 µm as measured with a laser diffraction particle size distribution analyzer (Model SALD-2300, manufactured by Shimadzu Corporation). The pulverized silica stone powder was subjected to a surface treatment using an ordinary method to obtain a surface-treated silica, using 4 parts by mass of 3-methacryloxypropyltrimethoxysilane relative to 100 parts by mass of the pulverized silica stone powder.
Surface-Treated Ba Glass Powder: Silane-treated Ba Glass Powder
A barium glass (E-3000, manufactured by ESSTECH) was pulverized with a ball mill to obtain a barium glass powder. The barium glass powder had an average particle diameter of 2.4 µm as measured with a laser diffraction particle size distribution analyzer (Model SALD-2300, manufactured by Shimadzu Corporation). The barium glass powder was subjected to a surface treatment using an ordinary method to obtain a surface-treated Ba glass powder, using 3 parts by mass of 3-methacryloxypropyltrimethoxysilane relative to 100 parts by mass of the barium glass powder.

SiO$_2$-Coated YBF: Silica-Coated Ytterbium Fluoride

A commercially available product (SG-YBF100WSCMP10 manufactured by Sukgyung AT; spherical in shape with an average particle diameter 110 nm) was used in its available form.

Examples 1 to 17 and Comparative Examples 1 to 4

The components were mixed in the compositions shown in Tables 1 and 2 at ordinary temperature (25° C.) to prepare primers (aqueous adhesive dental composition (X)) and pastes (curable dental composition (Y)). After being stored at a specific temperature for a specific time period, the paste and/or primer were used as samples in the tests conducted to examine their properties in the manner described below. The test results are presented in Tables 1 and 2, with "Shortly after preparation" indicating the results for primers and/or pastes stored at 25° C. for 1 day, and "After 3 weeks at 60° C." indicating the results for primers and/or pastes stored at 60° C. for 3 weeks.

Consistency

The paste of each Example and Comparative Example was degassed in vacuum, and charged into a syringe to prepare a sample for consistency test. With a 16 G (gauge) needle attached to the tip of the syringe, the piston was pushed to force out 0.8950 g of the sample into a lump at the center of a glass plate (5 cm×5 cm) in a 25° C. thermostatic chamber (40% humidity). With a 40 g glass plate (5 cm×5 cm) placed on the sample, the longest diameter and shortest diameter of the sample were measured through the glass plate after 120 seconds, and the arithmetic mean of the measured values was calculated as a consistency (mm). Here, "longest diameter of a sample" means the length of the longest axis through the center of the sample, and "shortest diameter of a sample" means the length of the axis orthogonal to the longest diameter, through the center of the sample. The difference in the consistency of the paste shortly after its preparation and after 3 weeks of storage at 60° C. is preferably 4 mm or less, more preferably 3 mm or less.

Stringiness

The paste of each Example and Comparative Example was charged into a syringe, and a 16 G needle was attached to the tip of the syringe. Thirty milligrams of paste was extruded onto a dental mixing paper measuring 59 mm in length and 83 mm in width, and the paste was observed for the presence or absence of stringiness as the needle tip was moved away from the paste. Here, the needle tip was moved at a rate of 1 s/5 cm. The paste was evaluated as being "Good" when it did not form a string, "Acceptable" when the paste formed a string but the string broke before it stretched 5 cm, and "Poor" when the string stretched more than 5 cm.

Flexural Strength and Elastic Modulus

A polyester film was laid over a glass slide, and a stainless-steel mold, measuring 2 mm in length, 25 mm in width, and 2 mm in depth, was mounted on the film. The paste sample of each Example and Comparative Example was charged into the mold, and another glass slide was pressed against the surface of the paste in the mold via another polyester film. The glass slides were then secured with 25 mm wide binder clips. With the sample being secured with the binder clips, light was applied to the sample at 5 points on each surface, 10 seconds at each point, using a dental visible-light irradiator (PenCure 2000, manufactured by J. Morita Corp.), and the sample was allowed to stand in a 37° C. thermostatic chamber for 15 minutes. The sample was then taken out of the thermostatic chamber, and the polymerized and cured product of the paste was removed from the mold. The product was immersed in 37° C. distilled water and stored therein for 24 hours to prepare a measurement sample for the flexure test. The sample was measured for flexural strength and elastic modulus in a three-point flexural test carried out with a span length (span) of 20 mm and a crosshead speed of 1 mm/min, using a universal tester (Shimadzu Corporation). The mean values of flexural strength and elastic modulus from five samples were determined as the flexural strength and elastic modulus of the paste.

Tensile Bond Strength to Bovine Dentin

The labial surfaces of bovine mandibular incisors were ground with a #80 silicon carbide paper (manufactured by Nihon Kenshi Co., Ltd.) under running water to obtain samples with exposed flat dentin surfaces. Each sample was further ground with a #1000 silicon carbide paper (manufactured by Nihon Kenshi Co., Ltd.) under running water to provide a smooth surface. After grinding, an adhesive tape, about 150 μm thick, having a round hole of 3 mm diameter was attached to the smooth surface to define the bonding area. The primer of each Example and Comparative Example was applied to the surface through the round hole with a brush, and, after 20 seconds, the surface was dried by blowing air until the applied primer was no longer flowable. Thereafter, the paste of each Example and Comparative Example was charged into the round hole, and, after attaching a 1 cm×1 cm PET film by pressing it against the paste, light was applied for 10 seconds to polymerize and cure the paste, using a dental visible-light irradiator (PenCure 2000, manufactured by J. Morita Corp.). After removing the PET film, the exposed surface was sandblasted with alumina under 2 MPa pressure to roughen the surface of the polymerized and cured paste. A cylindrical stainless steel rod (measuring 7 mm in diameter and 2.5 cm in length) was bonded at its one end face (circular end face) to the roughened surface, using a commercially available dental resin cement (PANAVIA® 21, manufactured by Kuraray Noritake Dental Inc.). The sample was allowed to stand at room temperature for 30 minutes, and immersed in distilled water. Here, a total of five samples was fabricated, and all samples were immersed in 37° C. distilled water and stored therein for 24 hours. After 24 hours, the samples were taken out of water, and measured for tensile bond strength using a universal tester (Shimadzu Corporation). Tensile bond strength was measured with the crosshead speed set at 2 mm/min. The mean value of measurements from five samples was determined as the tensile bond strength to bovine dentin.

Tensile Bond Strength to Zirconia

A cylindrical zirconia sintered body (inner diameter 12 mm×height 5 mm; fired at 1,500° C. for 2 hours) fabricated from a zirconia disc for CAD/CAM system (KATANA® zirconia HT, manufactured by Kuraray Noritake Dental Inc.) was ground with a #1000 silicon carbide paper (manufactured by Nihon Kenshi Co., Ltd.) under running water. After grinding, the surface of the zirconia sintered body was dried by removing water by air blowing. An adhesive tape, about 150 μm thick, having a round hole of 5 mm diameter was then attached to the dried, ground surface to define the bonding area. The zirconia sintered body was left unattended for 10 seconds with a ceramic primer (Clearfil® ceramic primer, manufactured by Kuraray Noritake Dental Inc.) applied to the surface, and the surface was dried by blowing air until the applied ceramic primer was no longer flowable. Thereafter, the paste of each Example and Comparative Example was charged into the round hole, and, after attaching a 1 cm×1 cm PET film by pressing it against the paste, light was applied for 10 seconds to cure the paste, using a dental visible-light irradiator (PenCure 2000, manufactured by J. Morita Corp.). After removing the PET film, the exposed surface was sandblasted with alumina under 2 MPa pressure to roughen the surface of the cured paste. A cylindrical stainless steel rod (measuring 7 mm in diameter and 2.5 cm in length) was bonded at its one end face (circular end face) to the roughened surface, using a commercially available dental resin cement (PANAVIA® 21, manufactured by Kuraray Noritake Dental Inc.). The sample was allowed to stand at room temperature for 30 minutes, and immersed in distilled water. Here, a total of five samples was fabricated, and all samples were immersed in 37° C. distilled water and stored therein for 24 hours. After 24 hours, the samples were taken out of water, and measured for tensile bond strength using a universal tester (Shimadzu Corporation). Tensile bond strength was measured with the crosshead speed set at 2 mm/min. The mean value of measurements from five samples was determined as the tensile bond strength to zirconia.

TABLE 1

| Aqueous adhesive dental composition (X) | | Ex. 1 A01 | Ex. 2 A02 | Ex. 3 A01 | Ex. 4 A01 | Ex. 5 A01 | Ex. 6 A01 | Ex. 7 A01 | Ex. 8 A01 | Ex. 9 A01 | Ex. 10 A01 | Ex. 11 A01 |
|---|---|---|---|---|---|---|---|---|---|---|---|---|
| Components (parts by mass) | | | | | | | | | | | | |
| Radical polymerizable monomer (a) containing acidic group | MDP | 15 | 15 | 15 | 15 | 15 | 15 | 15 | 15 | 15 | 15 | 15 |
| Polymerization accelerator (b) | VOAA | 0.5 | 0 | 0.5 | 0.5 | 0.5 | 0.5 | 0.5 | 0.5 | 0.5 | 0.5 | 0.5 |
|  | BMOV | 0 | 0.5 | 0 | 0 | 0 | 0 | 0 | 0 | 0 | 0 | 0 |
| Water (c) | $H_2O$ | 32 | 32 | 32 | 32 | 32 | 32 | 32 | 32 | 32 | 32 | 32 |
| Radical polymerizable monomer (d-1) containing no acidic group | HEMA | 35.5 | 35.5 | 35.5 | 35.5 | 35.5 | 35.5 | 35.5 | 35.5 | 35.5 | 35.5 | 35.5 |
|  | #801 | 15 | 15 | 15 | 15 | 15 | 15 | 15 | 15 | 15 | 15 | 15 |
| Polymerization inhibitor | BHT | 2 | 2 | 2 | 2 | 2 | 2 | 2 | 2 | 2 | 2 | 2 |
| Curable dental composition (Y) | | B01 | B01 | B02 | B03 | B04 | B05 | B06 | B07 | B08 | B09 | B10 |
| Hydrophilic radical polymerizable monomer (d-1) containing no acidic group | 3G | 27 | 27 | 0 | 27 | 27 | 27 | 27 | 37 | 32 | 15 | 40 |
|  | #801 | 10 | 10 | 10 | 10 | 10 | 10 | 10 | 0 | 10 | 10 | 10 |
|  | DEAA | 5 | 5 | 5 | 5 | 5 | 5 | 5 | 5 | 0 | 5 | 5 |
|  | DMAA | 0 | 0 | 0 | 0 | 0 | 0 | 0 | 0 | 0 | 0 | 0 |
| Hydrophobic radical polymerizable monomer (d-2) containing no acidic group | Bis-GMA | 0 | 0 | 50 | 0 | 0 | 0 | 0 | 0 | 0 | 0 | 0 |
|  | D2·6E | 0 | 0 | 35 | 0 | 0 | 0 | 0 | 0 | 0 | 0 | 0 |
|  | UDMA | 58 | 58 | 0 | 58 | 58 | 58 | 58 | 58 | 58 | 70 | 45 |
| Chemical polymerization initiator (e) | THP | 1 | 1 | 1 | 1 | 1 | 1 | 1 | 1 | 1 | 1 | 1 |
|  | CHP | 0 | 0 | 0 | 0 | 0 | 1 | 0 | 0 | 0 | 0 | 0 |
|  | BPO | 0 | 0 | 0 | 0 | 0 | 0 | 0 | 0 | 0 | 0 | 0 |
| Photopolymerization initiator (f) | CQ | 0.3 | 0.3 | 0.3 | 0.3 | 0.3 | 0.3 | 0.3 | 0.3 | 0.3 | 0.3 | 0.3 |
| Polymerization inhibitor | BHT | 0.21 | 0.21 | 0.21 | 0.21 | 0.21 | 0.21 | 0.21 | 0.21 | 0.21 | 0.21 | 0.21 |
| Other | JJA | 0.45 | 0.45 | 0.45 | 0.45 | 0.45 | 0.45 | 0.45 | 0.45 | 0.45 | 0.45 | 0.45 |
| Filler (g) | TMS-SiO$_2$-1 (g-1) | 270 | 270 | 270 | 270 | 270 | 0 | 270 | 0 | 0 | 0 | 0 |
|  | TMS-SiO$_2$-2 (g-2) | 0 | 0 | 0 | 0 | 0 | 0 | 0 | 270 | 270 | 270 | 270 |
| Filler (h) | Surface-treated silica | 0 | 0 | 0 | 0 | 0 | 270 | 0 | 0 | 0 | 0 | 0 |
|  | Surface-treated Ba glass powder | 0 | 0 | 0 | 0 | 0 | 0 | 0 | 0 | 0 | 0 | 0 |
|  | SiO$_2$ coated YBF | 30 | 30 | 30 | 30 | 30 | 30 | 30 | 30 | 30 | 30 | 30 |
| Properties | | | | | | | | | | | | |
| Consistency (mm) | Shortly after preparation | 22.8 | 22.3 | 19.6 | 23.6 | 24.1 | 22.5 | 23.2 | 25.1 | 28.7 | 18.5 | 31.7 |
|  | After 3 weeks at 60° C. | 24.7 | 23.9 | 21.0 | 25.1 | 24.9 | 23.5 | 24.1 | 26.1 | 30.1 | 19.8 | 33.0 |
| Stringiness | Shortly after preparation | Good | Good | Acceptable | Good | Good | Good | Good | Good | Acceptable | Acceptable | Good |
|  | After 3 weeks at 60° C. | Good | Good | Acceptable | Good | Good | Good | Good | Good | Acceptable | Acceptable | Good |
| Flexural strength (MPa) | Shortly after preparation | 128.7 | 133.6 | 126.5 | 123.9 | 135.9 | 128.4 | 135.2 | 129.8 | 103.2 | 134.9 | 122.4 |
|  | After 3 weeks at 60° C. | 135.1 | 137.3 | 130.2 | 120.4 | 130.5 | 122.5 | 137.1 | 127.6 | 106.7 | 132.1 | 120.1 |
| Elastic modulus (GPa) | Shortly after preparation | 5.7 | 5.8 | 6.0 | 5.4 | 5.7 | 5.3 | 5.8 | 5.6 | 4.3 | 5.9 | 4.6 |
|  | After 3 weeks at 60° C. | 5.8 | 5.8 | 6.1 | 5.6 | 5.6 | 5.2 | 5.7 | 5.4 | 4.5 | 5.8 | 4.5 |
| Tensile bond strength to bovine dentin (MPa) | Shortly after preparation | 28.1 | 25.6 | 26.3 | 24.3 | 28.1 | 22.5 | 25.3 | 13.1 | 22.5 | 19.4 | 22.3 |
|  | After 3 weeks at 60° C. | 27.3 | 26.3 | 22.5 | 24.7 | 23.3 | 24.3 | 25.8 | 15.6 | 20.9 | 23.5 | 20.4 |
| Tensile bond strength to zirconia (MPa) | Shortly after preparation | 34.5 | 33.2 | 30.2 | 32.1 | 33.1 | 29.8 | 32.2 | 30.6 | 20.1 | 35.8 | 30.5 |
|  | After 3 weeks at 60° C. | 35.9 | 32.1 | 28.9 | 30.6 | 30.5 | 27.8 | 33.1 | 29.6 | 21.3 | 34.2 | 31.2 |

TABLE 2

| | | | Ex. 12 A01 | Ex. 13 A01 | Ex. 14 A01 | Ex. 15 A01 | Ex. 16 A01 | Ex. 17 A01 | Com. Ex. 1 A01 | Com. Ex. 2 A01 | Com. Ex. 3 A01 | Com. Ex. 4 A01 |
|---|---|---|---|---|---|---|---|---|---|---|---|---|
| | Aqueous adhesive dental composition (X) | | | | | | | | | | | |
| Components (parts by mass) | Radical polymerizable monomer (a) containing acidic group | MDP | 15 | 15 | 15 | 15 | 15 | 15 | 15 | 15 | 15 | 15 |
| | Polymerization accelerator (b) | VOAA | 0.5 | 0.5 | 0.5 | 0.5 | 0.5 | 0.5 | 0.5 | 0.5 | 0 | 0.5 |
| | | BMOV | 0 | 0 | 0 | 0 | 0 | 0 | 0 | 0 | 0 | 0 |
| | Water (c) | $H_2O$ | 32 | 32 | 32 | 32 | 32 | 32 | 32 | 32 | 32 | 32 |
| | Radical polymerizable monomer (d) containing no acidic group | HEMA | 35.5 | 35.5 | 35.5 | 35.5 | 35.5 | 35.5 | 35.5 | 35.5 | 35.5 | 35.5 |
| | | #801 | 15 | 15 | 15 | 15 | 15 | 15 | 15 | 15 | 15 | 15 |
| | Polymerization inhibitor | BHT | 2 | 2 | 2 | 2 | 2 | 2 | 2 | 2 | 2 | 2 |
| | Curable dental composition (Y) | | B11 | B12 | B13 | B14 | B15 | B16 | B17 | B18 | B19 | B20 |
| | Hydrophilic radical polymerizable monomer (d-1) containing no acidic group | 3G | 27 | 27 | 27 | 27 | 15 | 40 | 27 | 27 | 27 | 27 |
| | | #801 | 10 | 10 | 10 | 10 | 10 | 10 | 10 | 0 | 10 | 10 |
| | | DEAA | 5 | 5 | 5 | 5 | 5 | 5 | 5 | 5 | 5 | 5 |
| | | DMAA | 0 | 0 | 0 | 0 | 0 | 0 | 0 | 0 | 0 | 0 |
| | Hydrophobic radical polymerizable monomer (d-2) containing no acidic group | Bis-GMA | 0 | 0 | 0 | 0 | 0 | 0 | 0 | 0 | 0 | 0 |
| | | D2·6E | 0 | 0 | 0 | 0 | 0 | 0 | 0 | 0 | 0 | 0 |
| | | UDMA | 58 | 58 | 58 | 58 | 70 | 45 | 58 | 58 | 58 | 58 |
| | Chemical polymerization initiator (e) | THP | 0.3 | 7 | 1 | 1 | 1 | 1 | 1 | 1 | 1 | 0 |
| | | CHP | 0 | 0 | 0 | 0 | 0 | 0 | 0 | 0 | 0 | 0 |
| | | BPO | 0 | 0 | 0 | 0 | 0 | 0 | 0 | 0 | 0 | 0 |
| | Photopolymerization initiator (f) | CQ | 0.3 | 0.3 | 0.1 | 3 | 0.3 | 0.3 | 0.3 | 0.3 | 0.3 | 0.3 |
| | Polymerization inhibitor | BHT | 0.21 | 0.21 | 0.21 | 0.21 | 0.21 | 0.21 | 0.21 | 0.21 | 0.21 | 0.21 |
| | Other | JJA | 0.45 | 0.45 | 0.15 | 4.5 | 0.45 | 0.45 | 0.45 | 0.45 | 0.45 | 0.45 |
| | Filler (g) | TMS-$SiO_2$-1 (g-1) | 0 | 0 | 0 | 0 | 0 | 0 | 0 | 0 | 270 | 270 |
| | | TMS-$SiO_2$-2 (g-2) | 270 | 270 | 270 | 270 | 70 | 370 | 0 | 0 | 0 | 0 |
| | Filler (h) | Surface-treated silica | 0 | 0 | 0 | 0 | 0 | 0 | 0 | 0 | 0 | 0 |
| | | Surface-treated Ba glass powder | 0 | 0 | 0 | 0 | 0 | 0 | 30 | 270 | 0 | 0 |
| | | $SiO_2$ coated YBF | 30 | 30 | 30 | 30 | 30 | 30 | 0 | 0 | 30 | 30 |
| Properties | Consistency (mm) | Shortly after preparation | 22.5 | 23.0 | 22.8 | 22.9 | 34.7 | 18.9 | 28.9 | 26.4 | 23.2 | 22.6 |
| | | After 3 weeks at 60° C. | 24.3 | 24.6 | 24.7 | 24.8 | 36.1 | 20.1 | 36.9 | 37.8 | 25 | 24.4 |
| | Stringiness | Shortly after preparation | Good | Good | Good | Good | Good | Good | Good | Acceptable | Good | Good |
| | | After 3 weeks at 60° C. | Good | Good | Good | Good | Good | Good | Good | Poor | Good | Good |
| | Flexural strength (MPa) | Shortly after preparation | 133.5 | 119.5 | 123.5 | 133.9 | 111.4 | 137.3 | 130.8 | 125.4 | 129.4 | 135.6 |
| | | After 3 weeks at 60° C. | 131.4 | 116.9 | 121.7 | 134.4 | 112.3 | 135.1 | No Curing | 126.9 | 126.5 | 133.2 |
| | Elastic modulus (GPa) | Shortly after preparation | 5.9 | 4.5 | 4.7 | 6.2 | 4.2 | 6.6 | 7.1 | 6.7 | 5.9 | 5.8 |
| | | After 3 weeks at 60° C. | 5.9 | 4.5 | 4.7 | 6.2 | 4.1 | 6.5 | No Curing | 6.4 | 5.7 | 5.7 |
| | Tensile bond strength to bovine dentin (MPa) | Shortly after preparation | 17.6 | 19.4 | 20.1 | 23.2 | 18.3 | 22.4 | 24.6 | 20.4 | 7.4 | 6.2 |
| | | After 3 weeks at .60° C. | 16.4 | 19.9 | 19.7 | 21.6 | 19.1 | 21.9 | 0 | 21.4 | 5.6 | 4.2 |
| | Tensile bond strength to zirconia (MPa) | Shortly after preparation | 34.9 | 24.5 | 23.5 | 22.5 | 28.1 | 36.7 | 34.2 | 28.4 | 29.4 | 31.2 |
| | | After 3 weeks at 60° C. | 33.2 | 25.8 | 22.7 | 25.3 | 25.8 | 34.6 | 0 | 25.6 | 32.7 | 35.6 |

As shown in Tables 1 and 2, in the dental adhesive material kits of Examples 1 to 17 according to the present invention, the consistency values did not differ greatly shortly after paste preparation and after 3-week storage at 60° C., and the difference was 3 mm or less. In contrast, the consistency after 3-week storage at 60° C. was considerably different in the pastes of Comparative Examples 1 and 2 that did not contain filler (g), and used the barium glass powder as the filler after a surface treatment with only the silane coupling agent (A). In the dental adhesive material kits of Comparative Examples 3 and 4 that did not contain polymerization accelerator (b) or chemical polymerization initiator (e), the tensile bond strength to bovine dentin shortly after paste preparation was considerably weaker than that observed in the dental adhesive material kits of the present invention, and the tensile bond strength after 3-week storage at 60° C. showed a large decrease of about 25 to 30% from the tensile bond strength shortly after preparation, though the paste properties were stable with a consistency change of 3 mm or less after 3-week storage at 60° C.

INDUSTRIAL APPLICABILITY

A dental adhesive material kit of the present invention is a dental adhesive material kit comprising an aqueous adhesive dental composition and a curable dental composition, and that exhibits high adhesive property to tooth structure and dental prosthesis through photopolymerization while maintaining good ease of handling with the paste properties that undergo little change during long storage. A dental adhesive material kit of the present invention ensures desirable mechanical strength for the cured product of the curable dental composition. A dental adhesive material kit of the present invention is preferred for use as a composite resin cement kit, a core cement kit, and a dental veneer cement kit, most preferably as a dental veneer cement kit.

The invention claimed is:

1. A dental adhesive material kit, comprising:
an aqueous adhesive dental composition; and
a curable dental composition,
wherein the aqueous adhesive dental composition comprises:
a radical polymerizable monomer comprising an acidic group;
a polymerization accelerator;
water; and
a radical polymerizable monomer containing no acidic group,
wherein the curable dental composition comprises:
a hydrophilic radical polymerizable monomer containing no acidic group;
a hydrophobic radical polymerizable monomer containing no acidic group;
a chemical polymerization initiator;
a photopolymerization initiator; and
a filler,
wherein the filler is treated with a surface treatment agent, and the filler has an average particle diameter of 0.01 to 50.0 μm,
wherein the surface treatment agent comprises:
a silane coupling agent represented by the following general formula [1],

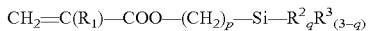

wherein:
$R^1$ is a hydrogen atom or a methyl group;
$R^2$ is an optionally substituted hydrolyzable group;
$R^3$ is an optionally substituted $C_1$ to $C_3$ alkyl group;
p is an integer of 1 to 13; and
q is 2 or 3; and
an organosilazane represented by the following general formula [2],

wherein:
$R^4$, $R^5$, and $R^6$ each independently represent a hydrogen atom or an optionally substituted $C_1$ to $C_3$ alkyl group;
at least one of $R^4$, $R^5$ and $R^6$ is an optionally substituted $C_1$ to $C_3$ alkyl group;
$R^7$, $R^8$, and $R^9$ each independently represent a hydrogen atom or an optionally substituted $C_1$ to $C_3$ alkyl group; and
at least one of $R^7$, $R^8$, and $R^9$ is an optionally substituted $C_1$ to $C_3$ alkyl group.

2. The dental adhesive material kit of claim 1, wherein:
$R^2$ is an unsubstituted hydrolyzable group,
$R^3$ is an unsubstituted $C_1$ to $C_3$ alkyl group,
$R^4$, $R^5$, and $R^6$ each independently represent a hydrogen atom or an unsubstituted $C_1$ to $C_3$ alkyl group,
at least one of $R^4$, $R^5$, and $R^6$ is an unsubstituted $C_1$ to $C_3$ alkyl group,
$R^7$, $R^8$, and $R^9$ each independently represent a hydrogen atom or an unsubstituted $C_1$ to $C_3$ alkyl group, and
at least one of $R^7$, $R^8$, and $R^9$ is an unsubstituted $C_1$ to $C_3$ alkyl group.

3. The dental adhesive material kit of claim 1, wherein $R^2$ is an unsubstituted $C_1$ to $C_6$ linear alkoxy group or an unsubstituted $C_1$ to $C_6$ branched alkoxy group.

4. The dental adhesive material kit of claim 1, wherein $R^1$ is a methyl group.

5. The dental adhesive material kit of claim 1, wherein p is 2 to 10.

6. The dental adhesive material kit of claim 1, wherein q is 3.

7. The dental adhesive material kit of claim 1, wherein the silane coupling agent is at least one selected from the group consisting of 2-(meth)acryloxyethyltrimethoxysilane, 3-(meth)acryloxypropyltrimethoxysilane, 4-(meth)acryloxybutyltrimethoxysilane, 5-(meth)acryloxypentyltrimethoxysilane, and 6-(meth)acryloxyhexyltrimethoxysilane.

8. The dental adhesive material kit of claim 1, wherein the organosilazane is at least one selected from the group consisting of 1,1,3,3-tetramethyldisilazane, 1,1,1,3,3,3-hexamethyldisilazane, and 1,1,1,3-pentamethyldisilazane.

9. The dental adhesive material kit of claim 1, wherein the silane coupling agent and the organosilazane have a silane coupling agent: organosilazane mole ratio of 1:1 to 1:20.

10. The dental adhesive material kit of claim 1, wherein the radical polymerizable monomer containing no acidic group comprises a second hydrophilic radical polymerizable monomer containing no acidic group.

11. The dental adhesive material kit of claim 1, wherein the hydrophilic radical polymerizable monomer containing no acidic group comprises a monofunctional (meth)acrylamide hydrophilic radical polymerizable monomer containing no acidic group.

12. The dental adhesive material kit of claim 1, wherein the polymerization accelerator is a period 4 transition metal compound.

13. The dental adhesive material kit of claim 1, wherein the chemical polymerization initiator is a hydroperoxide.

14. The dental adhesive material kit of claim 1, wherein the curable dental composition is a one-pack curable dental composition.

15. The dental adhesive material kit of claim 1, wherein the kit is a dental veneer cement kit.

* * * * *